United States Patent
Meuth et al.

(10) Patent No.: US 9,957,329 B2
(45) Date of Patent: May 1, 2018

(54) FACTOR XII INHIBITORS FOR THE TREATMENT OF NEUROLOGICAL INFLAMMATORY DISORDERS

(71) Applicants: CSL BEHRING GMBH, Marburg (DE); CSL LTD., Parkville, Victoria (AU); JULIUS-MAXIMILIANS-UNIVERSITAET-WUERZBURG, Wuerzburg (DE); WESTFAELISCHE WILHELMS-UNIVERSITAET MUENSTER, Muenster (DE)

(72) Inventors: Sven Meuth, Muenster (DE); Kerstin Goebel, Pfaffenhausen (DE); Christoph Kleinschnitz, Hettstadt (DE); Brent McKenzie, San Mateo, CA (US); Marc Nolte, Marburg (DE)

(73) Assignees: CSL Behring GmbH, Marburg (DE); CSL Ltd., Parkville (AU); Julius-Maximilians-Universitaet-Wuerzburg, Wuerzburg (DE); Westfaelische Wilhelms-Universitaet Muenster, Muenster (DE)

( * ) Notice: Subject to any disclaimer, the term of this patent is extended or adjusted under 35 U.S.C. 154(b) by 0 days. days.

(21) Appl. No.: 14/374,300

(22) PCT Filed: Jan. 31, 2013

(86) PCT No.: PCT/EP2013/051832
§ 371 (c)(1),
(2) Date: Jul. 24, 2014

(87) PCT Pub. No.: WO2013/113774
PCT Pub. Date: Aug. 8, 2013

(65) Prior Publication Data
US 2014/0378653 A1 Dec. 25, 2014

Related U.S. Application Data

(60) Provisional application No. 61/592,652, filed on Jan. 31, 2012.

(30) Foreign Application Priority Data

Jan. 31, 2012 (EP) ..................... 12153341

(51) Int. Cl.
| | |
|---|---|
| A61K 38/16 | (2006.01) |
| A61K 38/17 | (2006.01) |
| A61K 38/48 | (2006.01) |
| A61K 39/395 | (2006.01) |
| C07K 16/40 | (2006.01) |
| A61K 38/06 | (2006.01) |
| A61K 38/55 | (2006.01) |
| A61K 38/57 | (2006.01) |
| C07K 14/81 | (2006.01) |
| C07K 16/36 | (2006.01) |
| A61K 39/00 | (2006.01) |

(52) U.S. Cl.
CPC .............. *C07K 16/40* (2013.01); *A61K 38/06* (2013.01); *A61K 38/16* (2013.01); *A61K 38/1774* (2013.01); *A61K 38/48* (2013.01); *A61K 38/4846* (2013.01); *A61K 38/55* (2013.01); *A61K 38/556* (2013.01); *A61K 38/57* (2013.01); *A61K 39/395* (2013.01); *C07K 14/811* (2013.01); *C07K 16/36* (2013.01); *A61K 2039/505* (2013.01); *C07K 2317/56* (2013.01); *C07K 2317/565* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,252,714 A | 10/1993 | Harris et al. | |
| 6,403,077 B1 | 6/2002 | Strom et al. | |
| 6,613,890 B2 | 9/2003 | White et al. | |
| 7,083,784 B2 | 8/2006 | Dall'Acqua et al. | |
| 2004/0087778 A1 | 5/2004 | Feige et al. | |
| 2005/0176108 A1* | 8/2005 | Kim et al. | 435/70.21 |
| 2006/0024745 A1 | 2/2006 | Pritchard | |
| 2007/0135620 A1 | 6/2007 | Chamberlain et al. | |

(Continued)

FOREIGN PATENT DOCUMENTS

| | | |
|---|---|---|
| EP | 0 154 316 | 9/1989 |
| EP | 0 401 384 | 12/1990 |

(Continued)

OTHER PUBLICATIONS

Achiron et al., "Intravenous immunoglobulin treatment in multiple sclerosis: Effect on relapses", 1998, Neurology, pp. 398-402.*
Noseworthy et al., "Multiple Sclerosis", The New England Journal of Medicine, pp. 938-.*
National Institute of Neurological Disorders and Stroke, "Multiple Sclerosis: Hope Through Research", http://www.ninds.nih.gov/disorders/multiple_sclerosis/detail_multiple_sclerosis.htm?css=print; pp. 1-19; accessed Sep. 7, 2016.*
Morales et al., "The Pathology of Multiple Sclerosis: Evidence for Heterogeneity", Advanced in Neurology, Multiple Sclerosis and Demyelinating Diseases, vol. 98, 2006; pp. 27-45.*

(Continued)

*Primary Examiner* — Lianko G Garyu
(74) *Attorney, Agent, or Firm* — Finnegan, Henderson, Farabow, Garrett & Dunner, LLP

(57) ABSTRACT

This application relates to neurological inflammatory diseases, such as multiple sclerosis, and to methods of administering a Factor XII inhibitor to prevent, treat, or otherwise ameliorate the effects of a neurological inflammatory disease, such as multiple sclerosis. Agents and pharmaceutical compositions comprising agents which inhibit the activity of FXII are also provided.

14 Claims, 10 Drawing Sheets

(56) References Cited

U.S. PATENT DOCUMENTS

| | | | |
|---|---|---|---|
| 2008/0254039 A1 | 10/2008 | Nieswandt et al. | |
| 2010/0143344 A1 | 6/2010 | Baas et al. | |
| 2014/0199361 A1* | 7/2014 | Panousis et al. | 424/422 |

FOREIGN PATENT DOCUMENTS

| | | | |
|---|---|---|---|
| JP | 2002-508953 A | 3/2002 | |
| JP | 2010-505946 A | 2/2010 | |
| WO | WO 89/11865 | 12/1989 | |
| WO | WO 90/08835 | 8/1990 | |
| WO | WO 91/17258 | 11/1991 | |
| WO | WO 92/16221 | 10/1992 | |
| WO | WO 95/34326 | 12/1995 | |
| WO | WO 99/36439 | 7/1999 | |
| WO | WO 9936439 A1 * | 7/1999 | C07K 14/811 |
| WO | WO 2001/79271 | 10/2001 | |
| WO | WO 03/076567 A2 | 9/2003 | |
| WO | WO 2004/101740 A3 | 11/2004 | |
| WO | WO 2005/000892 A3 | 1/2005 | |
| WO | WO 2005/001025 A3 | 1/2005 | |
| WO | WO 2005/024044 A3 | 3/2005 | |
| WO | WO 2005/063808 A1 | 7/2005 | |
| WO | WO 2006/033386 A1 | 3/2006 | |
| WO | WO 2006/066878 | 6/2006 | |
| WO | WO 2007/122371 A1 | 1/2007 | |
| WO | WO 2008/044928 A1 | 4/2008 | |
| WO | WO 2008/098720 | 8/2008 | |
| WO | WO 2008098720 A1 * | 8/2008 | |
| WO | WO 2010/080538 A1 | 7/2010 | |
| WO | WO 2010/085682 A2 | 7/2010 | |
| WO | WO 2010/085682 A3 | 7/2010 | |
| WO | WO 2013/014092 A1 | 1/2013 | |

OTHER PUBLICATIONS

National Institute of Neurological Disorders and Stroke, "Transverse Myelitis Fact Sheer", http://www.ninds.nih.gov/disorders/transversemyelitis/detail_transversemyelitis.htm?css=print; pp. 1-9; accessed Sep. 7, 2016.*
National Institute of Neurological Disorders and Stroke, Neuromyelitis Optica Information Page. National Institute of Neurological Disorders and Stroke (NINDS); http://www.ninds.nih.gov/disorders/neuromyelitis_optica/neuromyelitis_optica.htm; accessed Sep. 7, 2016; pp. 1-4.*
Gale Encyclopedia of Medicine, "Multiple Sclerosis", 2006, pp. 1-13.*
"Prevent." Merriam-Webster.com. Merriam-Webster, n.d. Web. Apr. 11, 2017. p. 1.*
Morales et al., The Pathology of Multiple Sclerosis: Evidence for Heterogeneity, Adv Neurol 2006; 98:27-45.
Frohman et al., Multiple Sclerosis—The Plaque and Its Pathogenesis, N Engl J Med 2006; 354:942-55.
Ragonese et al., Mortality in Multiple Sclerosis: A Review, Eur J Neurol 2008;15:123-7.
Bergamaschi et al., Disabiiity and Mortality in a Cohort of Multiple Sclerosis Patients: A Reappraisal, Neuroepidemiolgy 2005; 25:15-18.
Polman et al., Diagnostic Criteria for Multiple Sclerosis: 2010 Revisions to the McDonald Criteria, Ann Neurol 2011; 69:292-302.
The International Multiple Sclerosis Genetics Consortium & The Wellcome Trust Case Control Consortium 2, Genetic Risk and a Primary Role for Cell-Mediated Immune Mechanisms in Multiple Sclerosis, Nature 2011; 476:214-9.
Stüve et al., Transiational Research in Neurology and Neuroscience 2010, Arch Neurol. 2010; 67:1307-15.
Herrmann et al., Glatiramer Acetate Attenuates Pro-Inflammatory T Cell Responses but Does Not Directly Protect Neurons from Inflammatory Cell Death, Am. J. Pathol. 2010; 177:3051-60.
Schmaier, The Elusive Physiologic Role of Factor XII, J. Clin, Invest. 2008; 118:3006-9.
Stavrou & Schmaier, Factor XII: What Does It Contribute to Our Understanding of the Physiology and Pathophysiology of Hemostasis & Thrombosis, Thromb. Res. 2010: 125:210-15.
Kleinschnitz et al., Targeting Coagulation Factor XII Provides Protection from Pathological Thrombosis in Cerebral Ischemia Without Interfering with Hemostasis, J. Exp. Med. 2006; 203:513-18.
Marik et al., Lesion Genesis in a Subset of Patients With Multiple Sclerosis: A Role for Innate Immunity?, Brain 2007; 130:2800-15 (26 pages).
Göbel et al., Blockade of the Kinin Receptor B1 Protects from Autoimmune CNS Disease by Reducing Leukocyte Trafficking, J. Autoimmunity 2011; 36:106-14.
Kurtzke, Historical and Clinical Perspectives of the Expanded Disability Status Scale, Neuroepidemiology 2008; 31:1-9.
Krishnamoorthy & Wekerle, Autoimmune Disease: Multiple Sclerosis, Eur. J. Immunol 2009; 39:2031-35.
Campos et al., Infestin, A Thrombin Inhibitor Presents in *Triatoma infestans* Midgut, A Chagas' Disease Vector: Gene Cloning, Expression and Characterization of the Inhibitor, Insect Biochem. Mol. Bio. 2002; 32:991-997.
Campos et al., Identification and Characterization of a Novel Factor XIIa Inhibitor in the Hematophagous Insect, *Triatoma infestoms* (Hemiptera: Reduviidae), FEBS Lett. 2004; 577:512-516.
Hagedorn, Factor XIIa Inhibitor Recombinant Human Albumin Infestin-4 Abolishes Occlusive Arterial Thrombus Formation Without Affecting Bleeding, Circulation 2010; 121:1510-17.
Laskowski and Kato, Protein Inhibitors of Proteinases, Ann. Rev. Biochem. 1980; 49:593-626.
Williams and Baird, DX-88 and HAE: A Developmental Perspective, Transfus Apheresis Sci. 2003; 29:255-258.
Isawa et al., A Mosquito Salivary Protein Inhibits Activation of the Plasma Contact System by Binding to Factor XII and High Molecular Weight Kininogen, J. Biol. Chem. 2002; 277(31):27651-27658.
Tans et al., Studies on the Effect of Serine Protease Inhibitors on Activated Contact Factors Application in Amidolytic Assays for Factor $XII_a$, Plasma Kallikrein and Factor $XI_a$, Eur. J. Biochem. 1987; 164:637-42.
Ravon et al., Monoclonal Antibody F1 Binds to the Kringle Domain of Factor XII and Induces Enhanced Susceptibility for Cleavage by Kallikrein, Blood 1995; 86(11):4134-43.
Pixley et al., A Monoclonal Antibody Recognizing an Icosapeptide Sequence in the Heavy Chain of Human Factor XII Inhibits Surface-catalyzed Activation, J. Biochem. 1987; 262, 10140-45.
Small et al., A Monoclonal Antibody that Inhibits Activation of Human Hageman Factor (Factor XII), Blood 1985; 65:202-10.
Nuijens et al., Activation of the Contact System of Coagulation by a Monoclonal Antibody Directed Against a Neodeterminant in the Heavy Chain Region of Human Coagulation Factor XII (Hageman Factor), J. Biol. Chem. 1989; 264:12941-49.
U.S. Appl. No. 61/510,801, filed Jul. 2, 2011.
Werle et al., Strategies to Improve Plasma Half Life Time of Peptide and Protein Drugs, Amino Acids 2006; 30:351-367.
Beattie et al., Structure and Evolution of Human α-Fetoprotein Deduced From Partial Sequence of Cloned cDNA, Gene 1982; 20:415-422.
Lichenstein et al., Afamin Is a New Member of the Albumin, α-Fetoprotein, and Vitamin D-binding Protein Gene Family, J. Biol. Chem. 1994; 269 (27):18149-18154.
Cooke & David, Serum Vitamin D-binding Protein is a Third Member of the Albumin and Alpha Fetoprotein Gene Family, J. Clin. Invest. 1985; 76:2420-2424.
Malik et al., Polyethylene Glycol (PEG)-modified Granulocyte-Macrophage Colony-stimulating Factor (GM-CSF) with Conserved Biological Activity, Exp. Hematol., 1992; 20:1028-1035.
Mathison et al., Nasal Route for Direct Delivery of Solutes to the Central Nervous System: Fact or Fiction?, J. Drug Target 1998; 5:415-41.
Chou et al., Distribution of Antihistamines Into the CSF Following Intranasal Delivery, Biopharm Drug Dispos. 1997;18(4):335-46.
Draghia et al., Gene Delivery into the Central Nervous System by Nasal Instillation in Rats, Gene Ther. 1995; 2(6):418-235.

(56) References Cited

OTHER PUBLICATIONS

Schuhmann et al., Stromal Interaction Molecules 1 and 2 Are Key Regulators of Autoreactive T Cell Activation in Murine Autoimmune Central Nervous System Inflammation, J. Immunol. 2010; 184:1536-42.
Sobel & Mitchell, Fibronectin in Multiple Sclerosis Lesions, Am. J. Pathol. 1989; 135:161-68.
Claudio et al., Evidence of Persistent Blood-Brain Barrier Abnormalities in Chronic-Progressive Multiple Sclerosis, Acta Neuropathol 1995; 90:228-38.
Schmaier, Assembly, Activation, and Physiologic Influence of the Plasma Kallikrein/Kinin System, Int. Immunopharmacol. 2008; 8:161-65.
Langrish et al., IL-23 Drives a Pathogenic T Cell Population That Induces Autoimmune Inflammation, J Exp Med. 2005; 201:233-40.
Qu et al., Interface Between Hemostasis and Adaptive Immunity, Curr Opin Immunol, 2010; 22(5), 634-42 (13 pages).
Lee et al., Compounds Acting on the Renin-Angiotensin-Aldosterone System as Potential Regulators of Autoimmune Neuroinflammation, Drugs of the Future 2010, 35(5); 393-398.
Osanai et al., Suppression of Experimental Allergic Encephalomyelitis with Liposome-Encapsulated Protease Inhibitor Therapy Through the Blood-Brain Barrier, Neurochemical Research, 1984, 9(10); 1407-1416 (abstract only).
Alonso et al., Temporal Trends in the Incidence of Multiple Sclerosis, Neurology 2008;71:129-135.
Graham et al., Chemokine-Like Receptor-1 Expression by Central Nervous System-Infiltrating Leukocytes and Involvement in a Model of Autoimmune Demyelinating Disease, Immunol. 2009; 183(10): 6717-6723 (21 pages).
Hart & Greaves, Chemerin Contributes to Inflammation by Promoting Macrophage Adhesion to VCAM-1 and Fibronectin through Clustering of VLA-4 and VLA-5, J Immunol. 2010; 185:3728-3739.
Muller et al., Platelet Polyphosphates are Proinflammatory and Procoagulant Mediators In Vivo, Cell. 2009; 139(6): 1143-1156 (22 pages).
Wachtfogel et al., Purified Plasma Factor XIIa Aggregates Human Neutrophils and Causes Degranulation, Blood, 1986; 67: 1731-1737.
Yednock et al., Prevention of Experimental Autoimmune Encephalomyelitis by Antibodies Against α4β1 Integrin, Nature 1992; 356: 63-66.
Francis G. E., Protein Modifications and Fusion Proteins, Focus on Growth Factors, May 1992, 3(2): 1-10.
European Search Report dated Aug. 7, 2012, for EP Application No. 12153341, 8 pages.
International Search Report dated Apr. 3, 1013, for PCT International Application No. EP 2013/051832, 14 pages.
Altschul et al., "Basic Local Alignment Search Tool," J. Mol. Biol., 215: 403-410 (1990).
Armour et al., "Recombinant Human IgG Molecules Lacking Fcg Receptor I Binding and Monocyte Triggering Activities," Eur. J. Immunol., 29: 2613-2624 (1999).
Kuhli et al., "Factor XII Deficiency: a Thrombophilic Risk Factor for Retinal Vein Occlusion," Am. J. Ophthalmol., 137: 459-464 (2004).
Citarella et al., "Structure/Function Anaiysis of Human Factor XII Using Recombinant Deletion Mutants: Evidence for an Additional Region Involved in the Binding to Negatively Charged Surfaces," Eur. J. Biochem., 238: 240-249 (1996).
Colman, "Chapter 6: Contact Activation Pathway: Inflammatory, Fibrinolytic, Anticoagulant, Antiadhesive, and Antiangiogenic Activities," from Hemostasis and Thrombosis: Basic Principles and Clinical Practice Fourth Edition, (R.W. Colman et al. Eds.), Lippincott Williams & Wilkins, Philadelphia, pp. 103-121 (2001).
Dall'Acqua et al., "Modulation of the Effector Functions of a Human IgG1 through Engineering of Its Hinge Region," J. Immunol., 177: 1129-1138 (2006).
Dors et al., "A Novel Sensitive Assay for Functional Factor XII Based on the Generation of Kallikrein-C1-Inhibitor Complexes in Factor XII-Deficient Plasma by Glass-Bound Factor XII," Thromb. Haemost., 67(6): 644-648 (1992).
Edelman et al., "The Covalent Structure of an Entire γG Immunoglobulin Molecule," PNAS, 63: 78-85 (1969).
Esnouf et al., "A Monoclonal Antioody Raised against Human β-factor XIIa which also Recognizes α-factor XIIa but not Factor XII or Complexes of Factor XIIa with C1 Esterase Inhibitor," Thromb. Haemost., 83: 874-881 (2000).
Extended European Search Report dated Jan. 12, 2012; for European Patent Application No. 11175105.3 (8 pages).
First Examination Report dated Nov. 24, 2014, for New Zealand Patent App. No. 619385 (2 pages).
Girolami et al., "The Occasional Venous Thromboses Seen in Patients with Severe (Homozygous) FXII Deficiency are Probably Due to Associated Risk Factors: A Study of Prevalence in 21 Patients and Review of the Literature." J. Thrombosis Thrombolysis, 17(2): 139-143 (2004).
Halbmayer et al., "Factor XII (Hageman Factor) Deficiency: A Risk Factor in the Development of Thromboembolism,"0 Wiener Medizinische Wochenschrift, 143: 43-50 (1993).
Han et al., "Increased Vascular Permeability in C1 Inhibitor—Deficient Mice Mediated by the Bradykinin Type 2 Receptor," J. Clin. Invest., 109: 1057-1063 (2002).
Hezareh et al., "Effector Function Activities of a Panel of Mutants of a Broadly Neutralizing Antibody Against Human Immunodeficiency Virus Type 1," J. Virol., 75(24): 12161-12168 (2001).
International Search Report and Written Opinion dated Aug. 28, 2012, for International Patent Application No. PCT/EP2012/064322, filed Jul. 20, 2012 (15 pages).
Devereux et al., "A Comprehensive Set of Sequence Analysis Program for the VAX," Nucl. Acids Res., 12(1): 387-395 (1984).
Zalevsky et al., "Enhanced Antibody Half-Life Improves in Vivo Activity," Nature Biotech., 28(2): 157-159 (2010).
Jostock et al., "Rapid Generation of Functional Human IgG Antibodies Derived from Fab-on-Phage Display Libraries," J. Immunol. Methods, 289: 65-80 (2004).
Koster et al., "John Hageman's Factor and Deep-Vein Thrombosis: Leiden Thrombophilia Study," Br. J. Haematol., 87: 422-424 (1994).
Kunkel et al., "Rapid and Efficient Site-Specific Mutagenesis without Phenotypic Selection," Methods Enzymol., 154: 367-382 (1987).
Mackman, "Role of Tissue Factor in Hemostasis, Thrombosis, and Vascular Development," Arterioscler. Thromb. Vasc. Biol., 24: 1015-1022 (2004).
Needleman et al., "A General Method Applicable to the Search for Similarities in the Amino Acid Sequence of Two Proteins," J. Mol. Biol., 48: 443-453 (1970).
Pearson et al., "Improved Tools for Biological Sequence Comparison," Proc. Natl. Acad. Sci. USA, 85: 2444-2448 (1988).
Ratnoff et al., "A Familial Hemorrhagic Trait Associated with a Deficiency of a Clot-promoting Fraction of Plasma," J. Clin. Invest., 34(4): 602-613 (1955).
Renné et al., "Defective Thrombus Formation in Mice Lacking Coagulation Factor XII," J. Exper. Med., 202(2): 271-281 (2005).
Schmaier et al., "Factor XII: New Life for an Old Protein," Throm. Haemost., 104: 915-918 (2010).
Shields et al., "High Resolution Mapping of the Binding Site on Human IgG1 for FcγγRI, FcγRII, FcγRIII, and FcRn and Design of IgG1 Variants with Improved Binding to the FcγR," J. Biol. Chem., 276(9): 6591-6604 (2001).
Sidhu et al., "[21] Phage Display for Selection of Novel Binding Peptides," Methods Enzymol., 328: 333-363 (2000).
Smith, "Comparison of Biosequences," Advances Applied Mathematics, 2: 482-489 (1981).
Warren et al., "High-Dose Antithrombin III in Severe Sepsis: A Randomized Controlled Trial," JAMA, 286: 1869-1878 (2001).
Zeerleder et al., "Reevaluation of the Incidence of Thromboembolic Complications in Congenital Factor XII Deficiency," Thromb. Haemost., 82: 1240-1246 (1999).

(56) References Cited

OTHER PUBLICATIONS

Patent Examination Report No. 1 dated Aug. 15, 2014, for Australian Patent App. No. 2012289001 (7 pages).

* cited by examiner

Fig. 1

```
MRYLLLLGLA AFSAVSAEKK DPPCVCPLIW KPVCGSDGQT YPSECILNCV KYALKKDIKV
AYQGICKHVT FAAEEEQEVE GWKGPCECPR ALHRVCGSDG NTYSNPCTLN CAKHERKSDL
VQVHEGPCSP DEHEFEDPCE CDNKFDPVCG TGEVTYRNLC HLECATFTTS PGVEVDYEGE
CLAETVLLEE NHCACPRVLH RVCGSDGNTY SNPCTLDCAK HEGKPDLVQV HEGPCDPNDH
DFEDPCECDN KFEPVCGTDH ITYSNLCHLE CAAFTTSPGV EVKYEGECHA EIMEQHQILK
SCICTKMYKP VCGTDGHTYP NLCVLKCRIS SKPGLKLAHV GKCGIGLLAV ETKEVRNPCA
CFRNYVPVCG SDGKTYGNPC MLNCAAQTKV PGLKLVHKGR CQRSDVEQF
```

SEQ ID NO: 1

Fig. 2

```
I4        EVRNPC-----ACFRNYVPVCGSDGKTYGNPCMLNCAAQTKVPGLKLV-HEGRC
SP: DSLGREAK--CYNELNGCTKIYDPVCGTDGNTYPNECVL-CFENRKRQTSILIQKSGPC
         *  |  *       *  | * ****|** ** * *|* *   |  *      *|    * *
K1: DSLGREVRNPC-----ACFRNYVPVCGTDGNTYPNECVL-CFENRKRQTSILIQKSGPC
         ******       **********|** ** * *|* *   |  *      *|    * *
K2: DSLGREVRNPC-----ACFRNYVPVCGTDGNTYGNECML-CAENRKRQTSILIQKEGPC
         ******       **********|** **** *** ** | *      *|   ** *
K3: DSLGREVRNPC-----ACFRNYVPVCGTDGNTYGNECMLNCAENRKRQTSILIQKEGPC
         ******       **********|** **** ****** |  *       *  | ** *
```

Fig. 3

```
DAHKSEVAHR FKDLGEENFK ALVLIAFAQY LQQCPFEDHV KLVNEVTEFA
KTCVADESAE NCDKSLHTLF GDKLCTVATL RETYGEMADC CAKQEPERNE
CFLQHKDDNP NLPRLVRPEV DVMCTAFHDN EETFLKKYLY EIARRHPYFY
APELLFFAKR YKAAFTECCQ AADKAACLLP KLDELRDEGK ASSAKQRLKC
ASLQKFGERA FKAWAVARLS QRFPKAEFAE VSKLVTDLTK VHTECCHGDL
LECADDRADL AKYICENQDS ISSKLKECCE KPLLEKSHCI AEVENDEMPA
DLPSLAADFV ESKDVCKNYA EAKDVFLGMF LYEYARRHPD YSVVLLLRLA
KTYETTLEKC CAAADPHECY AKVFDEFKPL VEEPQNLIKQ NCELFKQLGE
YKFQNALLVR YTKKVPQVST PTLVEVSRNL GKVGSKCCKH PEAKRMPCAE
DYLSVVLNQL CVLHEKTPVS DRVTKCCTES LVNRRPCFSA LEVDETYVPK
EFNAETFTFH ADICTLSEKE RQIKKQTALV ELVKHKPKAT KEQLKAVMDD
FAAFVEKCCK ADDKETCFAE EGKKLVAASQ AALGL
```

SEQ ID NO: 19

Fig. 5
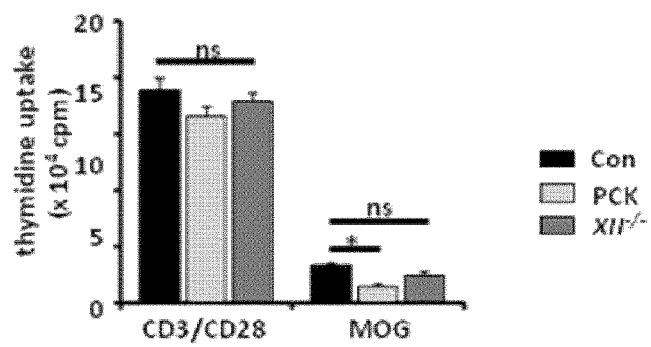
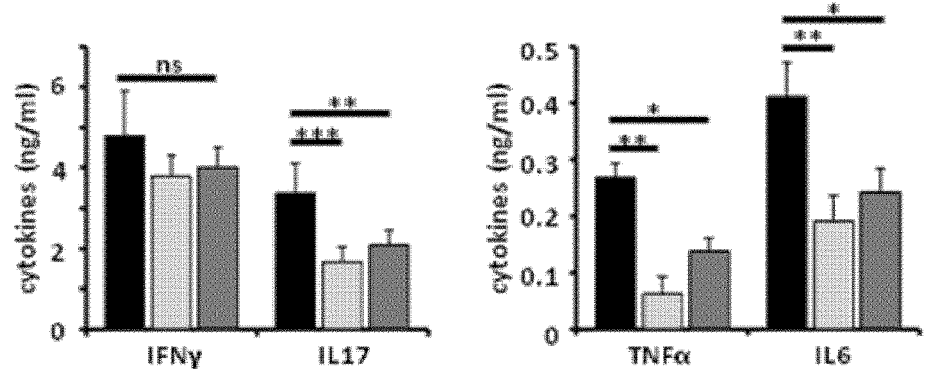

Fig. 6
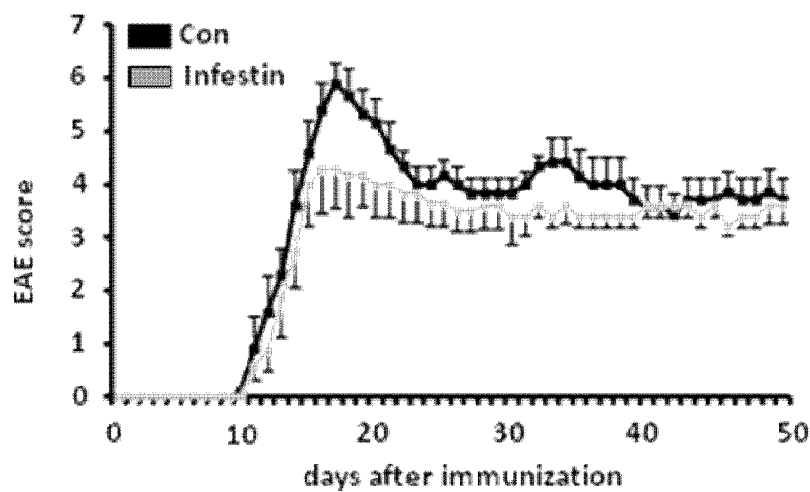
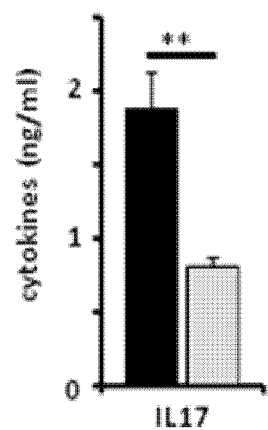

FACTOR XII INHIBITORS FOR THE TREATMENT OF NEUROLOGICAL INFLAMMATORY DISORDERS

This application is a national stage filing under 35 U.S.C. § 371 of International Application No. PCT/EP2013/051832, filed on Jan. 31, 2013, and claims the benefit of priority of U.S. Provisional Application No. 61/592,652, filed on Jan. 31, 2012, and of European Patent Application No. 12153341.8, filed on Jan. 31, 2012. All of these applications are incorporated herein by reference in their entirety.

This application relates to neurological inflammatory diseases, such as multiple sclerosis, and to methods of administering a Factor XII inhibitor to prevent, treat, or otherwise ameliorate the effects of a neurological inflammatory disease, such as multiple sclerosis. Agents and pharmaceutical compositions comprising agents which inhibit the activity of FXII are also provided.

Multiple sclerosis (MS) is part of a spectrum of neurological inflammatory diseases that include infiltration of immune cells, demyelination, and axonal/neuronal damage as part of their pathology. The World Health Organization (ICD-9-CM Diagnosis code 340) describes MS as a chronic disease characterized by the presence of numerous areas of demyelination in the central nervous system with symptoms such as weakness, incoordination, paresthesis, and speech disturbances. MS and other diseases like it are caused by autoimmune attack in which inflammatory cells invade the nervous system leading to demyelination and tissue destruction. (Morales et al., Adv Neurol 2006; 98:27-45; Frohman et al., N Engl J Med 2006; 354:942-55) The histopathological corollaries are MS plaques with cellular infiltrates (T cells, B cells, macrophages), which are ultimately believed to cause the oligodendroglial and axonal damage. As the destructive process progresses, the demyelination leads to impairment of cognitive function. (Ragonese et al., Eur J Neurol 2008; 15:123-7; Bergamaschi et al., Neuroepidemiology 2005; 25:15-18).

Demyelination is the loss of the myelin sheath that forms an insulating layer around neural axons. Myelin is produced by different cell types depending on the anatomic location: oligodendrocytes myelinate the axons of the central nervous system (CNS), while Schwann cells myelinate peripheral axons. Myelin is composed of several proteins and lipids, including myelin basic protein (MBP), myelin oligodendrocyte glycoprotein (MOG), proteolipid protein (PLP), galactocerebroside (GalC), and sphinogomyelin.

Signs and symptoms of demyelinating diseases vary depending on the location of the demyelination. Some common signs and symptoms include visual problems (double vision, nystagmus, or vision loss), tingling or numbness (paresthesia), speech impairment, memory loss, heat sensitivity, muscle spasms, muscle weakness, and loss of coordination or balance.

The name "multiple sclerosis" refers to the multiple scars ("scleroses"), or lesions, that form in the brain and spinal cord in areas where the myelin is lost. The disease pattern of MS can vary. According to the U.S. National Multiple Sclerosis Society, there are four standardized subtypes: (1) relapsing remitting, (2) secondary progressive, (3) primary progressive, and (4) progressive relapsing. Relapsing remitting is the most common initial course of disease and is characterized by attacks separated by periods of remission that may last for months to years, during which there are no new signs of disease. Secondary progressive disease, as the name implies, begins as relapsing-remitting MS, but definite periods of remission eventually disappear. The primary progressive subtype describes disease in which there is never a meaningful remission after the initial onset. In progressive relapsing disease, there is a steady neurological decline from onset, but in addition there are superimposed attacks.

Multiple sclerosis can be diagnosed using the 2010 revisions to the McDonald criteria, which rely on magnetic resonance imagining (MRI) coupled with the clinical presentation. (Polman et al., Ann Neurol 2011; 69:292-302.) Generally, a patient presenting with two or more attacks or with two or more objective clinical lesions is considered to have MS without need for additional clinical evidence. In patients with fewer attacks or fewer demonstrable lesions, diagnosis is based on objective demonstration of dissemination of lesions in space and/or time by clinical or clinical and diagnostic (MRI) findings.

The etiology of MS is unknown, but it is generally accepted that it is an autoimmune disease in which the body's immune system destroys myelin in the CNS. (International Multiple Sclerosis Genetics Consortium; Wellcome Trust Case Control Consortium 2, Nature 2011; 476:214-9.) A prerequisite for immune cell infiltration into the CNS is a disruption in the blood-brain barrier that normally protects the CNS from infiltration. This process results in CNS inflammation, which is a second pathological hallmark of MS. As with many autoimmune diseases, MS is more common in women than in men, affecting approximately 3 people per 100,000. (Alonso, 2008.) In addition to MS, there are other demyelinating inflammatory diseases. For example, other demyelinating inflammatory diseases of the central nervous system include the idiopathic inflammatory demyelinating diseases, transverse myelitis, and neuromyelitis optica (Devic's disease). Inflammatory demyelination may also occur in the peripheral nervous system: examples include Guillain-Barré syndrome, chronic inflammatory demyelinating polyneuropathy, Miller Fisher Syndrome, and anti-MAG peripheral neuropathy.

Current treatments for MS are based on the autoimmune nature of the disease and were developed, at least in part, based on experiments using experimental autoimmune encephalomyelitis (EAE) animal models. (Stüve et al., Arch Neurol. 2010; 67:1307-15.) Fingolimod, approved by the FDA in 2010 for treatment in relapsing forms of MS, is a phospholipid that acts by sequestering lymphocytes, the immune cells thought to mediate the destruction of myelin. (GILENYA (fingolimod), prescribing information, July 2011 revision.) Fingolimod also received orphan drug designation (EU/3/09/718) in Europe in 2010 for treatment of chronic inflammatory demyelinating polyneuropathy. Older treatments for MS include interferon beta-1a and interferon beta-1b, and glatiramer acetate, which are immunomodulators. (Herrmann et al., Am. J. Pathol. 2010; 177:3051-60; Stüve et al., Arch Neurol. 2010; 67:1307-15.) Natalizumab, a humanized monoclonal antibody against integrin α4, was approved in 2004 for treatment of patients with relapsing forms of MS. (TYSABRI (natalizumab) prescribing information, August 2011 revision.) It is generally used as a second line therapy because its use is associated with an increased risk of life-threatening viral infection (PML, progressive multifocal leukoencephalopathy). Natalizumab blocks the binding of leukocytes to certain cellular adhesion molecules involved in passage of cells from the blood into tissues. Thus, natalizumab is thought to work by preventing the passage of immune cells into the CNS, thereby preventing further destruction of myelin. Mitoxantrone is an agent that blocks DNA synthesis and so may reduce the ability of lymphocytes to proliferate.

Although each of the currently approved therapies show some effectiveness at decreasing at least the number of attacks in relapsing forms of MS, their effectiveness is limited and in many cases is associated with significant side effects, making long-term therapy impractical. Thus, there is a great unmet biomedical need for additional therapies.

Factor XII (FXII) is a serine protease that is involved in the activation of the intrinsic coagulation cascade. It was identified in 1955 as a clotting factor that is activated by contact with polyanions (contact activation). In vivo these surfaces include inorganic polyphosphates (PolyP) that are secreted by activated platelets, (Muller et.al., 2009), endothelial cell surfaces (qC1qR), cytokeratin1, urokinase-plasminogen activation receptor (u-PAR, CD87), articular cartilage, skin, fatty acids, endotoxin, proteoglycans (heparan sulfate, chondroitin sulfate E, mast cell heparin), and amyloid proteins. (Schmaier, 2008.) Once FXII has been activated to form FXIIa, there is a positive feedback reaction in which FXIIa activates circulating FXII. A variety of FXII inhibitors, ranging from small molecules to proteins, are available. Although FXII is the initiating factor in the intrinsic pathway, Factor XII deficiency does not contribute to bleeding because the extrinsic (tissue factor) pathway is the primary pathway for clot formation.

Despite its well-established role in the intrinsic pathway, the physiologic role of Factor XII remains unclear. (Schmaier, J. Clin. Invest. 2008; 118:3006-9; Stavrou & Schmaier, Thromb. Res. 2010.) FXII is involved in the inflammatory process through the formation of bradykinin via the kinin-kallikrein system. Bradykinin contributes to the classical inflammatory parameters of redness, heat, swelling, and pain, which are caused by activation of endothelial cells to increase vascular permeability, production of nitric oxide, and mobilization of arachidonic acid, as well as by stimulating sensory nerve endings. It is also involved in pathological thrombosis in ischemia. (Kleinschnitz et al., J. Exp. Med. 2006; 203:513-8.) Yet another role of FXII is in chemotaxis, aggregation, and degranulation of neutrophils. (Wachtfogel et. al., 1986.) It can also enhance monocyte production of the pro-inflammatory cytokine IL-1, and is involved in the complement system.

SUMMARY OF CERTAIN EMBODIMENTS

Thus, FXII is involved in multiple complex, pathways, but it remains unclear whether FXII is essential in vivo for any of these pathways. For example, humans that are deficient in FXII do not suffer from abnormal bleeding diathesis, even during major surgical procedures. (Schmaier, J. Clin. Invest. 2008; 118:3006-9.) Further, although FXII can be involved in fibrin deposition, which has been reported to be activated in MS (Marik et al. Brain 2007; 130:2800-15), and in the activation of bradykinin which may also contribute to MS (Göbel et al. J. Autoimmunity 2011; 36:106-14), it is unclear whether it is the FXII-dependent pathway that causes these effects, or another pathway that shares the same end result, such as fibrin deposition by the extrinsic coagulation pathway. Accordingly, direct demonstration of a role for FXII in any of the pathological features of MS is currently lacking.

Although the role of Factor XII (FXII) in inflammatory demyelination was previously unrecognized, the embodiments of this application provide inhibitors of FXII to prevent, treat, or ameliorate multiple sclerosis and other forms of inflammatory demyelination. The application provides methods of administering a Factor XII inhibitor to prevent, treat, or otherwise ameliorate the effects of a neurological inflammatory disease, including multiple sclerosis. A "FXII inhibitor" refers to inhibitors of either or both of Factor XII and activated Factor XII (FXIIa).

Accordingly, in one aspect, the invention provides methods of preventing, treating, or ameliorating a neurological inflammatory disease comprising administering to a subject in need thereof a therapeutically effective amount of a Factor XII (FXII) inhibitor, thereby preventing, treating, or ameliorating the neurological inflammatory disease.

In another aspect, the invention provides an inhibitor of Factor XII for the use of preventing, treating, or ameliorating a neurological inflammatory disease comprising administering to a subject in need thereof a therapeutically effective amount of a Factor XII (FXII) inhibitor.

In yet another aspect, the invention provides the use of a Factor XII inhibitor for preventing, treating, or ameliorating a neurological inflammatory disease comprising administering to a subject in need thereof a therapeutically effective amount of a Factor XII (FXII) inhibitor.

In various embodiments of any of the aspects of the invention, the FXII inhibitor may comprise the wild type infestin-4 polypeptide sequence (SEQ ID NO: 2), or a variant thereof, wherein the variant comprises: (a) the N-terminal amino acids 2-13 of SEQ ID NO: 2; and at least one and up to five amino acid mutations outside the N-terminal amino acids that result in differences from the wild type infestin-4 sequence; and/or (b) six conserved cysteine residues; and homology of at least 70% to the wild type infestin-4 sequence.

In various embodiments of any of the aspects of the invention, the FXII inhibitor may comprise SPINK-1 (SEQ ID NO: 3), which is mutated to include the N-terminal amino acids 2-13 of SEQ ID NO: 2, or a variant of the mutated SPINK-1, wherein a variant comprises (a) the N-terminal amino acids 2-13 of SEQ ID NO: 2; and at least one and up to five amino acid mutations outside the N-terminal amino acids that result in differences from the wild type SPINK-1 sequence and which increase the homology of the variant to the wild type infestin-4 sequence; and/or (b) six conserved cysteine residues; and homology of at least 70% to the wild type SPINK-1 sequence.

In various embodiments of any of the aspects of the invention, the FXII inhibitor may comprise SPINK-1, or the SPINK-1 mutants K1, K2, or K3 (SEQ ID NOS: 3, 4, 5, or 6, respectively).

In various embodiments of any of the aspects of the invention, the FXII inhibitor may comprise H-D-Pro-Phe-Arg-chloromethylketone (PCK), AT III, angiotensin converting enzyme inhibitor, C1 inhibitor, aprotinin, alpha-1 protease inhibitor, antipain ([(S)-1-carboxy-2-phenylethyl]-carbamoyl-L-Arg-L-Val-Arginal), Z-Pro-Pro-aldehyde-dimethyl acetate, DX88, leupeptin, inhibitors of prolyl oligopeptidase such as Fmoc-Ala-Pyr-CN, corn-trypsin inhibitor, mutants of the bovine pancreatic trypsin inhibitor, ecotin, YAP (yellowfin sole anticoagulant protein), *Cucurbita maxima* trypsin inhibitor-V, or *Curcubita maxima* isoinhibitors.

In various embodiments of any of the aspects of the invention, the FXII inhibitor may comprise an anti-FXII antibody or antigen binding fragment thereof, wherein the antibody binds to FXII and inhibits its activity and/or activation.

In those embodiments in which the FXII inhibitor is an antibody or antigen binding fragment thereof, the anti-FXII antibody or antigen binding fragment thereof may comprise (a) a VH region comprising heavy chain CDR1 as set forth in SEQ ID NO: 9, heavy chain CDR2 as set forth in SEQ ID NO: 11, and heavy chain CDR3 as set forth in SEQ ID NO: 13; and/or (b) a VL region comprising light chain CDR1 as set forth in SEQ ID NO: 14, light chain CDR2 as set forth in SEQ ID NO: 15, and light chain CDR3 as set forth in SEQ ID NO: 17. In some of these embodiments, the anti-FXII antibody or antigen-binding fragment thereof comprises (a) a VH region comprising heavy chain CDR1 as set forth in SEQ ID NO: 9, heavy chain CDR2 as set forth in SEQ ID NO: 10, and heavy chain CDR3 as set forth in SEQ ID NO: 12; and/or (b) a VL region comprising light chain CDR1 as set forth in SEQ ID NO: 14, light chain CDR2 as set forth in SEQ ID NO: 15, and light chain CDR3 as set forth in SEQ ID NO: 16. In certain embodiments, the anti-FXII antibody or antigen-binding fragment thereof comprises a VH region comprising SEQ ID NO: 7 and a VL region comprising SEQ ID NO: 8. In any of the embodiments involving an antibody, the anti-FXII antibody may be an IgG. In any of the embodiments, the anti-Factor XII/XIIa monoclonal antibody or antigen-binding fragment thereof may inhibit human Factor XIIa-alpha by more than 50% when used at a molar ratio of FXIIa-alpha to antibody of 1:0.2.

In various embodiments of any of the aspects of the invention, the FXII inhibitor may be linked to a half-life enhancing polypeptide that is albumin, afamin, alpha-fetoprotein, vitamin D binding protein, human albumin or a variant thereof, an immunoglobulin or a variant thereof, PEG, or a variant thereof, or an Fc of an IgG. In some of these embodiments, the half-life enhancing polypeptide is linked to the FXII inhibitor via a linker. In some of the embodiments involving a linker, the linker can be (a) cleavable; (b) cleavable by a coagulation protease of the intrinsic, extrinsic, or common coagulation pathway; and/or (c) cleavable by Factor XIIa.

In various embodiments of any of the aspects of the invention, the FXII inhibitor may comprise a human albumin-linker-FXII fusion protein.

In various embodiments of any of the aspects of the invention, the neurological inflammatory disease may be multiple sclerosis (MS). In some of those embodiments involving MS, the MS can be relapsing remitting multiple sclerosis. In other embodiments involving MS, the MS can be primary progressing multiple sclerosis.

In various embodiments of any of the aspects of the invention, the neurological inflammatory disease may be transverse myelitis.

In various embodiments of any of the aspects of the invention, the neurological inflammatory disease may be neuromyelitis optica (Devic's disease).

Additional objects and advantages of the embodiments in the application appear in part in the following description and in part will be obvious from the description, or they may be learned in practice. The objects and advantages of the embodiments will manifest themselves by means of the elements and combinations particularly pointed out in the appended claims.

DESCRIPTION OF THE DRAWINGS

FIG. 1 presents the amino acid sequence of infestin (SEQ ID NO: 1).

FIG. 2 compares the amino acid sequences of infestin-4 (SEQ ID NO: 2), SPINK-1 (SEQ ID NO: 3) and three SPINK-1 variants (K1 (SEQ ID NO: 4), K2 (SEQ ID NO: 5), and K3 (SEQ ID NO: 6)). * denotes identical amino acids, and | denotes similar amino acids with regard to the Infestin-4 sequence. The underlined sequence of infestin-4 was used to replace 15 amino acids of SPINK-1 to generate K1. Variants K2 and K3 were generated by additional point mutations (amino acids underlined) on the K1 sequence.

FIG. 3 presents the amino acid sequence of human albumin (SEQ ID NO: 19).

FIG. 4A presents $FXII^{-/-}$ mice compared to control mice (Con). FIG. 4B presents $FXI^{-/-}$ mice compared to control mice (Con). FIGS. 4C and 4D present scores for mice treated with the FXII inhibitor PCK compared to controls starting from the day of immunization (FIG. 4C) or from day 12 (FIG. 4D).

FIG. 5A depicts the number of inflammatory foci, FIG. 5B the demyelinated area/slice, and FIG. 5C the axon counts in control (left bar), PCK treated (middle bar), and $FXII^{-/-}$ mice (right bar). Examples of histologic comparisons between control (Con) and PCK-treated mice are presented for each bar graph. FIG. 5D presents proliferation of splenocytes in response to CD3/CD28 or MOG stimulation. FIG. 5E summarizes cytokine secretion in splenocytes from control (left bar), PCK treated (middle bar), and $FXII^{-/-}$ mice (right bar).

FIG. 6A presents the EAE scores as a function of time for mice treated with the FXII inhibitor, rHA-Infestin-4. FIG. 6B compares the levels of the cytokine IL-17 in control (left bar) versus rHA-Infestin-4-treated (right bar) mice.

DETAILED DESCRIPTION

Figure 4:
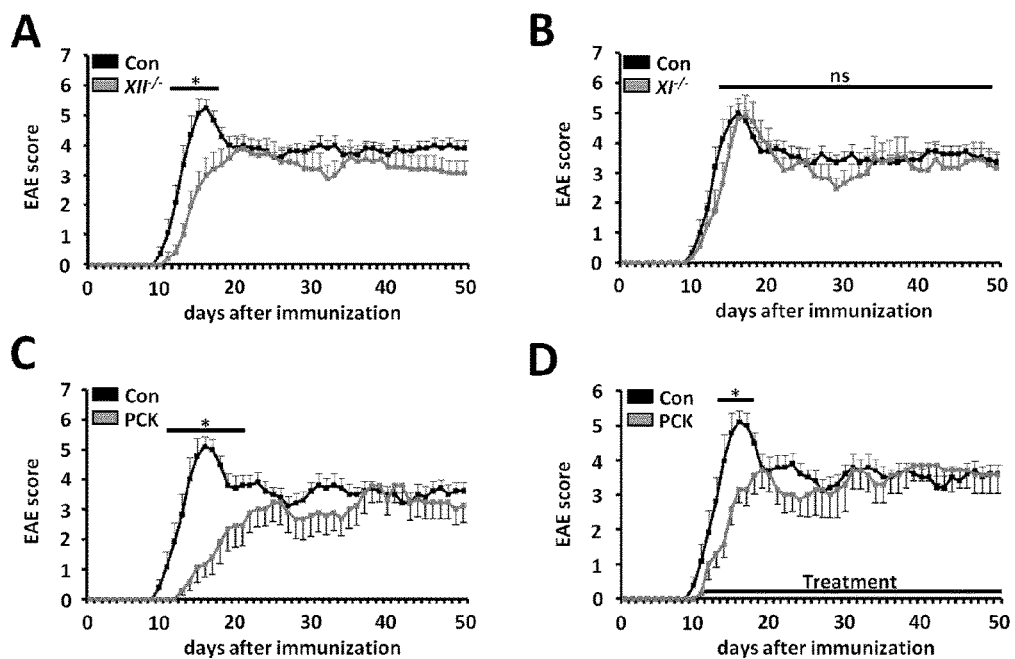
FIG. 4A-D depict the EAE score of mice as a function of time.

The embodiments of the application pertain to methods comprising administering at least one Factor XII (FXII) inhibitor to a patient to prevent, treat, or otherwise ameliorate the effects of a neurological inflammatory disease.

One advantage of the embodiments of the application is that FXII inhibitors may have an improved safety profile compared to other drugs, since they are expected to be well-tolerated. In addition, since FXII is involved in several physiological cascades, one or more of which may be involved in inflammatory demyelinating diseases such as MS, FXII inhibitors may have a better efficacy profile compared to single target therapies.

I. Inflammatory Demyelinating Diseases

One aspect the invention relates to methods of preventing, treating, or otherwise ameliorating the effects of an inflammatory demyelinating disease, comprising administering to a subject in need thereof at least one Factor XII (FXII) inhibitor, to thereby prevent, treat, or ameliorate the effects of the neurological inflammatory disease. Accordingly, the invention also provides pharmaceutical compositions comprising a Factor XII inhibitor and a pharmaceutically acceptable excipient or carrier for use in preventing, treating, or ameliorating the effects of an inflammatory demyelinating disease.

As used here, the terms "treat" and "treating" do not require a complete elimination of symptoms, and these terms are not equivalent to "cure" or "curing." Instead, "treat" and "treating" mean that at least one sign or symptom of the disease has been reduced, inhibited, lessened, or delayed. In some embodiments, the signs or symptoms are one or more of the primary or secondary endpoints described below. In certain embodiments, "treat" or "treating" can also include ameliorating the effects of the disease. In general, however, "ameliorating the effects" means that some aspect of the disease that reflects an impairment of the patient's function is improved. Functional assessments can be made using well-established criteria for the disease, including the use of the Kurtzke Expanded Disability Status Score (EDSS) (Kurtzke J F, Neuroepidemiol. 2008; 31:1-9) for multiple sclerosis (MS), as described below. "Preventing," as used here, means either administration of therapy to a subject that is known to be at risk for developing an inflammatory demyelinating disease or, in those diseases that remit and then relapse, "preventing" can mean inhibiting relapse in a patient who is in remission. As noted below for MS, "preventing" also means that a patient that satisfies some, but not all, of the diagnostic criteria for MS but does not progress to overt disease fully meeting the diagnostic criteria.

The terms "neurological inflammatory disease" and "inflammatory demyelinating disease" are used essentially interchangeably to refer to a condition in a human patient, or in an animal, in which there is inflammation of one or more areas of brain or spinal cord. The terms are not fully equivalent, however, and the skilled artisan will appreciate that a neurological inflammatory disease does not necessarily require demyelination, although demyelination often develops following the inflammation. Multiple sclerosis is one example of an inflammatory demyelinating disease in humans. In a variety of animals, including mice, rats, and monkeys, inflammatory demyelination can be induced experimentally by several different immunization strategies that are well-known and are accepted as models of human disease. (Reviewed in Krishnamoorthy & Wekerle, Eur. J. Immunol 2009; 39:2031-35.) Two different immunization strategies are presented in the Examples. The resulting induced disease, experimental autoimmune encephalomyelitis (EAE), is another example of an inflammatory demyelinating disease, albeit an experimental disease and accordingly confined to non-human subjects.

In some embodiments, the inflammatory demyelinating disease is a disease of the central nervous system (CNS). Exemplary diseases include, but are not limited to, multiple sclerosis, idiopathic inflammatory demyelinating diseases, transverse myelitis, and neuromyelitis optica (Devic's disease).

In some embodiments, the inflammatory demyelinating disease is a disease of the peripheral nervous system. Exemplary diseases include, but are not limited to, Guillain-Barré syndrome, chronic inflammatory demyelinating polyneuropathy, Miller Fisher syndrome, and anti-MAG peripheral neuropathy.

In certain embodiments, the invention provides methods of preventing, treating, or ameliorating the effects of multiple sclerosis, comprising administering to a subject in need thereof a therapeutically effective amount of at least one Factor XII inhibitor, thereby preventing or treating multiple sclerosis or ameliorating the effects of multiple sclerosis. Accordingly, the invention also provides pharmaceutical compositions comprising a Factor XII inhibitor and a pharmaceutically acceptable excipient or carrier for use in preventing or treating multiple sclerosis, or for ameliorating the effects of multiple sclerosis.

In those embodiments involving multiple sclerosis, subjects with MS can be diagnosed using the "McDonald criteria," which rely on magnetic resonance imagining (MRI) coupled with the clinical presentation. (Polman et al., Ann Neurol 2011; 69:292-302.) Generally, a patient presenting with two or more attacks or with two or more objective clinical lesions is considered to have MS without need for additional clinical evidence. In patients with fewer attacks or fewer demonstrable lesions, diagnosis is based on objective demonstration of dissemination of lesions in space and/or time by clinical or clinical and diagnostic (MRI) findings. Clinical evidence of dissemination of lesions in space is demonstrated by one or more T2 lesions in at least two of four of the following areas of the central nervous system: periventricular, juxtacortical, infratentorial, or spinal cord. Dissemination of lesions in time is demonstrated by either a new T2 and/or gadolinium-enhancing lesion on follow-up MRI or the simultaneous presence of asymptomatic gadolinium-enhancing and non-enhancing lesions at any time. Primary progressive MS is diagnosed in subjects with one year of disease progression (including retrospective), plus two or more of: A) evidence of dissemination in space based on one or more T2 lesions in the brain in at least one area characteristic of MS (periventricular, juxtacortical, or infratentorial), or B) evidence for dissemination in space in the spinal cord based on greater that two T2 lesions, and C) the presence of oligoclonal bands and/or elevated IgG index in the cerebrospinal fluid. (Polman et al., Ann Neurol 2011; 69:292-302.)

In some embodiments, the patient has, or has had, at least one clinical attack or at least one objective clinical lesion, but has not presented with a sufficient number of clinical attacks and objective clinical lesions to establish a diagnosis of multiple sclerosis using the McDonald criteria. Such a patient is a patient "at risk" for multiple sclerosis and administering a FXII inhibitor to a patient that is "at risk" for MS can be used to prevent MS in the sense that the subject does not progress to the point that a diagnosis of MS can be made under the McDonald criteria. Accordingly, in one embodiment there is provided a method of preventing multiple sclerosis comprising administering at least one FXII inhibitor to a subject at risk for multiple sclerosis, thereby preventing multiple sclerosis. Likewise, the invention also provides pharmaceutical compositions comprising a Factor XII inhibitor and a pharmaceutically acceptable excipient or carrier for use in preventing multiple sclerosis in a subject at risk for multiple sclerosis.

In those embodiments involving a subject that has been diagnosed with multiple sclerosis, the subjects may be further categorized based on the disease course into subjects with (1) relapsing remitting, (2) secondary progressive, (3) primary progressive, and (4) progressive relapsing MS.

Thus, the invention provides in certain embodiments methods of preventing, treating, or ameliorating the effects of multiple sclerosis, comprising administering to a patient diagnosed with relapsing remitting MS a therapeutically effective amount of at least one Factor XII inhibitor, thereby preventing or treating the relapsing remitting MS or ameliorating the effects of the relapsing remitting MS. In addition, the invention provides pharmaceutical compositions comprising a Factor XII inhibitor and a pharmaceutically acceptable excipient or carrier for use in preventing, treating, or ameliorating the effects of relapsing remitting multiple sclerosis.

In additional embodiments, the invention provides methods of preventing, treating or ameliorating the effects of multiple sclerosis, comprising administering to a patient diagnosed with secondary progressive MS a therapeutically effective amount of at least one Factor XII inhibitor, thereby preventing or treating the secondary progressive MS or ameliorating the effects of the secondary progressive MS. In addition, the invention provides pharmaceutical compositions comprising a Factor XII inhibitor and a pharmaceutically acceptable excipient or carrier for use in preventing, treating, or ameliorating the effects of secondary progressive multiple sclerosis.

In still other embodiments, the invention provides methods of preventing, treating, or ameliorating the effects of multiple sclerosis, comprising administering to a patient diagnosed with primary progressive MS a therapeutically effective amount of at least one Factor XII inhibitor, thereby preventing or treating the primary progressive MS or ameliorating the effects of the primary progressive MS. In addition, the invention provides pharmaceutical compositions comprising a Factor XII inhibitor and a pharmaceutically acceptable excipient or carrier for use in preventing, treating, or ameliorating the effects of primary progressive multiple sclerosis.

In further embodiments, the invention provides methods of preventing, treating, or ameliorating the effects of multiple sclerosis, comprising administering to a patient diagnosed with progressive relapsing MS a therapeutically effective amount of at least one Factor XII inhibitor, thereby preventing or treating the progressive relapsing MS or ameliorating the effects of the progressive relapsing MS. In addition, the invention provides pharmaceutical compositions comprising a Factor XII inhibitor and a pharmaceutically acceptable excipient or carrier for use in preventing, treating, or ameliorating the effects of progressive relapsing multiple sclerosis.

One example of ameliorating the effects of or treating any of the types of MS is a reduction in the disability status of the subject or an increase in the time to disability progression. The disability status can be evaluated (or scored) using the Kurtzke Expanded Disability Status Score (EDSS). (Kurtzke J F, Neuroepidemiol 2008; 31:1-9.) For example, an inhibitor reduces the disability score if it reduces the time to onset of "sustained increase in disability," defined as an increase of at least 1 point on the EDSS from baseline EDSS≥1.0 that was sustained for 12 weeks, or at least a 1.5 point increase on the EDSS from baseline EDSS=0 that was sustained for 12 weeks. Other examples of ameliorating the effects of or treating any of the types of MS can be measured by MRI: for example, a decrease in the median number of new or newly enlarging T2-hyperintense lesions over a defined period, e.g., 12, 24, 36, or 48 months; or a decrease in the number of T1 gadolinium-enhancing lesions over a defined period, e.g., 12, 24, 36, or 48 months.

In general, criteria that can be used to show that a FXII inhibitor according to the invention is treating MS or ameliorating the effects of MS include the following outcomes, either alone or in any subcombination: a decrease in extent of number of contrast-enhancing MRI lesions; a decrease in the Sustained Accumulation of Disability (SAD) rating; a decrease in the occurrence of relapse; an increase in the time to relapse; an increase in the proportion of patients who are relapse-free at, for example, 1, 2, 3, or more years after initial treatment; a decrease in the rate of cerebral atrophy on brain scan; a decrease in MRI T2 lesion volume; change in cerebrospinal fluid ("CSF") osteopontin levels; improvement in expanded disability status scale (EDSS); improvement in Timed 25-foot Walk (T25FW) test; improvement in Multiple Sclerosis Impairment Score (MSIS); improvement in Multiple Sclerosis Functional Composite Short Form 36 Health Survey (SF36); an improvement in the levels of neurofilament heavy chain in the cerebrospinal fluid; an improvement in the levels of myelin basic protein in cerebrospinal fluid; an improvement in normalized brain volume (NBV), grey matter volume (GMV), and/or white matter volume (WMV); an improvement in Magnetization transfer ratio (MTR) in whole brain, lesions, normal-appearing grey matter (NAGM), or normal-appearing white matter (NAWM); an improvement in Diffusion transfer imaging (DTI) in FA and ADC in lesions, GM and NAWM; an improvement in CSF cell count; an improvement in in IgG-index; an improvement in CSF nitrogen oxide metabolites; an improvement in the CSF-serum albumin concentration quotient; an improvement in CSF CXCL13 levels; an improvement in Matrix metalloproteinase-9 (MMP-9) levels; a decrease in new Gadolinium-enhancing lesions (GdEL); a decrease in volume of lesions on T2-weighted MRI images, a decrease in the number of new or enlarging lesions on T2-weighted MRI images; any combination of these criteria; or any subcombination of these criteria. For any of the criteria, the criteria can be judged relative to the time at which treatment began.

In those embodiments involving a relapsing form of MS, a FXII inhibitor according to the invention also treats or ameliorates MS if it reduces the annualized relapse rate or increases the percentage of patients remaining relapse-free for a defined period, such as, 6 months, 12 months, 18 months, 24 months, 36 months, 48 months, or 60 months (or for any time in between).

The EAE model can be used to determine whether a particular FXII inhibitor will prevent, treat, or ameliorate multiple sclerosis. EAE models are accepted animal models of MS and have been used to develop drugs approved by the FDA for treatment of multiple sclerosis. (E.g., Stüve et al., Arch. Neurol. 2010; 67:1307-15; Yednock et al., Nature 1992.) Accordingly, if a particular FXII inhibitor shows activity in one or more EAE model, such as those described in the examples, the skilled artisan would expect that a FXII inhibitor also shows activity in preventing, treating, or ameliorating the effects of multiple sclerosis. It is worth noting, however, that inactivity in an EAE model does not preclude activity in multiple sclerosis. For example, one early treatment for MS, interferon beta, was not very effective in the EAE model. (Stüve et al., Arch. Neurol. 2010; 67:1307-15.)

II. FXII Inhibitors

The terms "Factor XII" and "FXII" each refer to either or both of Factor XII and activated Factor XII (FXIIa). Thus "FXII inhibitor" includes inhibitors of either or both of FXII and FXIIa. Further, anti-FXII antibodies include antibodies that bind to and inhibit either or both of FXII and FXIIa. The term "FXII inhibitor" is also meant to include an inhibitor of FXII that is linked to a half-life extending polypeptide, which in some embodiments includes a linker.

In some embodiments, the FXII inhibitor is a direct inhibitor of FXII. The term "direct" inhibitor means an inhibitor that acts via contact (e.g., binding) with FXII (or FXIIa). In contrast, an indirect inhibitor may act without contacting FXII (or FXIIa) protein; for example, an antisense RNA can be used to decrease expression of the FXII gene, but it does not interact directly with FXII protein. Thus, an indirect inhibitor, in contrast to a direct inhibitor, acts upstream or downstream from the FXII protein. Some examples of direct inhibitors are presented below. The FXII inhibitors are generally non-endogenous inhibitors; that is, they are not inhibitors that occur naturally in the body of a subject with inflammatory demyelinating disease.

A. Infestin-4

In one embodiment, the application provides a FXII inhibitor comprising infestin domain 4, "infestin-4." Recently, infestin-4 was reported to be a novel inhibitor of activated FXII (FXIIa). Infestins are a class of serine protease inhibitors derived from the midgut of the hematophagous insect, *Triatoma infestans*, a major vector for the parasite *Trypanosoma cruzi*, known to cause Chagas disease. (Campos I T N et al. 32 *Insect Biochem. Mol. Bio.* 991-997, 2002; Campos I T N et al. 577 *FEBS Lett.* 512-516, 2004.) This insect uses these inhibitors to prevent coagulation of ingested blood. The full length precursor polypeptide sequence of infestin is provided in FIG. 1 (SEQ ID NO: 1). The infestin gene encodes 4 domains that result in proteins that can inhibit different factors in the coagulation pathway. In particular, domain 4 encodes a protein (infestin-4) that is a strong inhibitor of FXIIa. Infestin-4 has been administered in mice without bleeding complications. (WO 2008/098720; Hagedorn et al., Circulation 2010; 121:1510-17.)

Accordingly, in one embodiment, there is provided a FXII inhibitor that comprises a variant of infestin-4. In another embodiment, FXII inhibitors comprise infestin domain 4, and optionally infestin domains 1, 2, and/or 3. These proteins are known to be potent inhibitors of FXII. (See WO 2008/098720; also see Campos I T N et al. 577 *FEBS Lett.* 512-516, 2004.) In one embodiment, the FXII inhibitor is a (His)$_6$-tagged infestin-4 construct. In another embodiment, the FXII inhibitor is a fusion protein consisting of albumin-linker-infestin-4. In one embodiment, the albumin-linker-infestin-4 is the rHA-Infestin-4 protein described in Hagedorn et al. Circulation 2010; 121:1510-17. Examples of infestin inhibitors of FXII are described in WO 2008/098720 and Hagedorn et al. Circulation 2010; 121:1510-17.

As used here, the term "variant" of infestin refers to a polypeptide with an amino acid mutation, wherein the "mutation" is defined as a substitution, a deletion, or an addition, to the wild type infestin-4 sequence, wherein such changes do not alter the functional ability of the polypeptide to inhibit FXII. The term "variant" includes fragments of the wild type or mutated infestin-4 sequence. Further examples of such variants are provided below.

In one embodiment, an infestin-4 variant comprises the amino acid sequence VRNPCACFRNYV (residues 2-13 of SEQ ID NO: 2) from the amino terminal of the wild type infestin-4 sequence (see underlined sequence in FIG. 2), and at least one and up to five amino acid mutations outside the N-terminal amino acids that result in differences from the wild type infestin-4 sequence, and/or six conserved cysteine residues, and/or homology of at least 70% to the wild type infestin-4 sequence. Therefore in some embodiments, a variant of infestin-4 comprises the conserved N-terminal region of amino acids 2-13 of the wild type infestin-4 sequence, and at least one and up to five amino acid mutations outside these conserved N-terminal amino acids that result in differences from the wild type infestin-4 sequence. As used here, the term "outside the N-terminal amino acids" of an infestin variant refers to any amino acid along the polypeptide chain of the variant other than the contiguous stretch of amino acids that comprises the sequence VRNPCACFRNYV, i.e., amino acids 2-13 from SEQ ID NO: 2. In another embodiment, an infestin-4 variant comprises six conserved cysteine residues and has homology of at least 70% to the wild type infestin-4 sequence. In one embodiment, the six conserved cysteine residues are amino acids at positions 6, 8, 16, 27, 31, and 48 of the wild type infestin-4 sequence, SEQ ID NO: 2 (see FIG. 2). In one embodiment, the variant comprises the final conserved cysteine at position 48. In other embodiments, the exact positions of the cysteine residues, and relative positions to each other, may change from positions 6, 8, 16, 27, 31, and 48 of the wild type infestin-4 sequence due to insertions or deletions in the infestin-4 variant. Nevertheless, in these embodiments, an infestin-4 variant comprises all six cysteines and may share 70%, 75%, 85%, 90%, 91%, 92%, 93%, 94%, 95%, 96%, 97%, 98% or 99%, or any percentage in between homology to the wild type infestin-4 sequence.

In one embodiment, the FXII inhibitor comprises a variant of the wild type infestin-4 polypeptide sequence (SEQ ID NO: 2), wherein the variant comprises the N-terminal amino acids 2-13 of SEQ ID NO: 2; at least one and up to five amino acid mutations outside said N-terminal amino acids that result in differences from the wild type Infestin-4 sequence; six conserved cysteine residues; and homology of at least 70% to the wild type Infestin-4 sequence.

In infestin-4 variant embodiments, a variant of infestin-4 is characterized in that it inhibits FXII. The functional activity of inhibiting FXII may be assessed for example, through in vitro and/or in vivo characterization, including direct assays to test inhibition of FXII enzyme activity, prolonged coagulation time, i.e. activated partial thromboplastin time (aPTT; a clinical clotting test that addresses the intrinsic pathway of coagulation), or in vivo methods that evaluate coagulation.

Further examples of infestin-4 variants are SPINK-1 mutants, which are described below.

B. SPINK-1 Mutants

One embodiment involves FXII inhibitors for therapeutic use in humans. A human protein with high similarity to infestin-4 may be employed. For example, the human protein with the highest similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of serine protease inhibitors. Many proteins from different species have been described. (Laskowski M and Kato I, 49 *Ann. Rev. Biochem.* 593-626, 1980.)

Based on the wild type SPINK-1 sequence (SEQ ID NO: 3) different variants may be generated in order to increase homology of the SPINK-1 sequence to Infestin-4. In one embodiment, SPINK-1 is mutated to comprise the N-terminal amino acids 2-13 of SEQ ID NO: 2, which is thought to be important for FXII inhibitory function. The polypeptide sequence, referred to as K1, is given in SEQ ID NO: 4 and FIG. 2.

In one embodiment, a variant of the mutated SPINK-1 also comprises N-terminal amino acids 2-13 of the wild type Infestin-4 sequence (SEQ ID NO: 2), and at least one and up to five amino acid mutations outside said N-terminal amino acids that result in differences from the wild type SPINK-1 sequence and which increase the homology of the variant to the wild type infestin-4 sequence. In another embodiment, a variant of mutated SPINK-1 comprises six conserved cysteine residues and has homology of at least 70% to the wild type SPINK-1 sequence. A mutation may be a substitution, a deletion, or an addition. As defined above, the term "outside the N-terminal amino acids" refers to any amino acid along the polypeptide chain of the variant other than the contiguous stretch of amino acids that is comprised of the sequence VRNPCACFRNYV, i.e., amino acids 2-13 of SEQ ID NO: 2. The term "variant" includes fragments of said mutated SPINK-1 sequence. In one embodiment, the six conserved cysteine residues may be amino acids at positions 9, 16, 24, 35, 38, and 56 of the wild type SPINK-1 sequence (SEQ ID NO: 3, see FIG. 2). In one embodiment, the variant comprises the final conserved cysteine. In another embodiment, the exact positions of the cysteines, and relative positions to each other, may change from positions 9, 16, 24, 35, 38, and 56 of the wild type SPINK-1 sequence due to insertions or deletions in the SPINK-1 variant. Nevertheless, in these embodiments, a SPINK-1 variant comprises all six cysteines. In embodiments, a SPINK-1 variant is also characterized in that it inhibits FXII.

In one embodiment, the FXII inhibitor comprises a variant of SPINK-1 (SEQ ID NO: 3), wherein the SPINK-1 variant comprises the N-terminal amino acids 2-13 of SEQ ID NO: 2; at least one and up to five amino acid mutations outside said N-terminal amino acids that result in differences from the wild type SPINK-1 sequence and which increase the homology of the variant to the wild type infestin-4 sequence; six conserved cysteine residues; and homology of at least 70% to the wild type SPINK-1 sequence.

Examples of SPINK-1 variants are given and are named K1, K2, and K3 (SEQ ID NOS: 4, 5 and 6, respectively). In SPINK-1 variants K2 and K3, further amino acid substitutions outside of the N-terminus were made relative to K1 in order to increase homology to infestin-4, wherein the variants are also characterized in that they inhibit FXII activity. See WO 2008/098720. FIG. 2 shows the amino acid sequence of these variants and the degree of changes to the SPINK-1 wild type sequence. In the case of the SPINK-1 variant K3, five amino acid substitutions increase homology to infestin-4. Thus in embodiments, a SPINK-1 variant may share 70%, 75%, 85%, 90%, 91%, 92%, 93%, 94%, 95%, 96%, 97%, 98% or 99% or any percentage in between homology with the wild type SPINK-1 sequence.

C. Other FXII Inhibitors

Other inhibitors of FXII, including inhibitors of both FXII and FXIIa, are described in WO2006/066878. Accordingly, in some embodiments the FXII inhibitor is antithrombin 111 (AT 111), angiotensin converting enzyme inhibitor, C1 inhibitor, aprotinin, alpha-1 protease inhibitor, antipain ([(S)-1-carboxy-2-phenylethyl]-carbamoyl-L-Arg-L-Val-Arginal), Z-Pro-proaldehyde-dimethyl acetate, DX88 (Dyax Inc., 300 Technology Square, Cambridge, Mass. 02139, USA; cited in: Williams A and Baird L G, 29 *Transfus Apheresis Sci.* 255-258, 2003), leupeptin, inhibitors of prolyl oligopeptidase such as Fmoc-Ala-Pyr-CN, corn-trypsin inhibitor, mutants of the bovine pancreatic trypsin inhibitor, ecotin, yellowfin sole anticoagulant protein, *Cucurbita maxima* trypsin inhibitor-V including *Curcurbita maxima* isoinhibitors, or Hamadarin (as disclosed by Isawa H et al., 277 *J. Biol. Chem.* 27651-27658, 2002).

In still other embodiments, the FXII inhibitor is H-D-Pro-Phe-Arg-chloromethylketone (PCK). (Tans et al., Eur. J. Biochem. 1987; 164:637-42; Kleinschnitz et al., J Exp Med. 2006; 203:513-8.)

In yet other embodiments, the FXII inhibitor is an analogue of Kunitz Protease Inhibitor domain of amyloid precursor protein as disclosed in U.S. Pat. No. 6,613,890 in columns 4 through 8.

D. FXII Antibodies

In other embodiments, the FXII inhibitor is an anti-FXII antibody that binds to FXII and inhibits FXII activation and/or activity. Anti-FXII antibodies have been described, for example in WO 2006/066878, and in Rayon et al., 1 *Blood* 4134-43, 1995. Other monoclonal antibodies (mAbs) to human Factor XII include the B7C9 mAb described by Pixley et al (*J Biol Chem* 1987; 262, 10140-45), a mAb described by Small et al (*Blood* 1985; 65:202-10); the mAbs F1 and F3 described by Nuijens et al (*J. Biol. Chem.* 1989; 264:12941-49); the B6F5, C6B7, and D2E10 mAbs against the light chain of FXII described in WO89/11865; a mAb that selectively binds FXIIa-β over FXII described in WO90/08835; and the anti-FXII antibody OT-2 described in WO91/17258.

Additional anti-Factor XII/FXIIa monoclonal antibodies and antigen-binding fragment thereof are described in U.S. provisional application No. 61/510,801, filed Jul. 22, 2011, which is incorporated herein by reference. Those antibodies have a more than 2 fold higher binding affinity to human Factor XIIa-beta than to human Factor XII and are capable of inhibiting the amidolytic activity of human Factor XIIa. In some embodiments, the antibody or antigen-binding fragment has one or more of the following features: (a) binds murine FXII/FXIIa; (b) comprises a heavy chain variable (VH) region which is more than 85% identical to the sequence of SEQ ID NO: 7; (c) comprises a light chain variable (vL) region which is more than 85% identical to the sequence of SEQ ID NO: 8; (d) comprises heavy chain CDR1 at least 80% identical to the sequence of SEQ ID NO: 9, and/or heavy chain CDR2 at least 60% identical with SEQ ID NO: 10, and/or heavy chain CDR3 at least 80% identical to the sequence of SEQ ID NO: 12; (e) comprises light chain CDR1 at least 50% identical with SEQ ID NO: 14, and/or light chain CDR2 of SEQ ID NO: 15, and/or light chain CDR3 with the sequence A-$X_1$-W-$X_2$-$X_3$-$X_4$-$X_5$-R-$X_6$-$X_7$ wherein $X_1$ can be A or S, $X_5$ can be L or V, the other $X_n$s can be any amino acid (SEQ ID NO: 17); (f) binds human Factor XIIa-beta with a $K_D$ of better than $10^{-8}$M; (g) competes with infestin-4, for binding to human Factor XIIa-beta; or (h) is a human IgG or variant thereof, preferably human IgG4 or variant thereof.

In other embodiments, the anti-FXII antibody is an IgG antibody that binds human FXII and comprises (a) a VH region comprising heavy chain CDR1 as set forth in SEQ ID NO: 9, heavy chain CDR2 as set forth in SEQ ID NO: 11, and heavy chain CDR3 as set forth in SEQ ID NO: 13; and/or (b) a VL region comprising light chain CDR1 as set forth in SEQ ID NO: 14, light chain CDR2 as set forth in SEQ ID NO: 15, and light chain CDR3 as set forth in SEQ ID NO: 17. A heavy chain CDR2 comprising SEQ ID NO: 11 comprises the sequence GI$X_1$$X_2$$X_3$$X_4$$X_5$$X_6$TVYADS-VKG, wherein $X_1$ is R, N or D, $X_2$ is P, V, I, or M; $X_3$ is S, P, or A; $X_4$ is G, L, V, or T; $X_5$ can be any amino acid, preferably $X_5$ is G, Y, Q, K, R, N, or M; and $X_6$ is T, G, or S. A heavy chain CDR3 comprising SEQ ID NO: 13 comprises the sequence ALPRSGYL$X_1$$X_2$$X_3$$X_4$YYYY-ALDV, wherein $X_1$ is I, M or V; $X_2$ is S or K; $X_3$ is P, K, T, or H; and $X_4$ is H, N, G, or Q. A light chain CDR3 comprising SEQ ID NO: 17 comprises the sequence A$X_1$W$X_2$$X_3$$X_4$$X_5$R$X_6$$X_7$, wherein $X_1$ is A or S; $X_2$ is D, Y, E, T, W, E, or S; $X_3$ is A, N, I, L, V, P, Q, or E; $X_4$ is S, D, P, E, Q, or R; $X_5$ is L or V; $X_6$ is G, L, or K; and $X_7$ is V, A, D, T, M, or G.

In other embodiments, the anti-FXII antibody antigen-binding fragment is a fragment of an IgG antibody that binds human FXII and comprises (a) a VH region comprising heavy chain CDR1 as set forth in SEQ ID NO: 9, heavy chain CDR2 as set forth in SEQ ID NO: 10, and heavy chain CDR3 as set forth in SEQ ID NO: 12; and/or (b) a VL region comprising light chain CDR1 as set forth in SEQ ID NO: 14, light chain CDR2 as set forth in SEQ ID NO: 15, and light chain CDR3 as set forth in SEQ ID NO: 16.

In one embodiment, the anti-FXII antibody or antigen-binding fragment thereof is the antibody "3F7" used in Example 3. Sequences of the variable regions and CDRs of 3F7 are presented in Table 1.

TABLE 1

| Region | Amino acid sequence |
|---|---|
| VH | EVQLLESGGGLVQPGGSLRLSCAASGFTFSKYI MQWVRQAPGKGLEWVSGIRPSGGTTVYADSVKG RFTISRDNSKNTLYLQMNSLRAEDTAVYYCARA LPRSGYLISPHYYYYALDVWGQGTTVTVSS (SEQ ID NO: 7) |
| VL | QSELTQPPSASGTPGQRVTISCSGSSSNIGRNY VYWYQQVPGTAPKLLIYSNNQRPSGVPDRFSGS KSGTSASLVISGLRSEDEADYYCAAWDASLRGV FGGGTKLTVLG (SEQ ID NO: 8) |
| HCDR 1 (Kabat 31-35) | KYIMQ (SEQ ID NO: 9) |
| HCDR 2 (Kabat 50-65) | GIRPSGGTTVYADSVKG (SEQ ID NO: 10) |
| HCDR 3 (Kabat 95-102) | ALPRSGYLISPHYYYYALDV (SEQ ID NO: 12) |
| LCDR 1 (Kabat 24-34) | SGSSSNIGRNYVY (SEQ ID NO: 14) |
| LCDR 2 (Kabat 50-56) | SNNQRPS (SEQ ID NO: 15) |
| LCDR 3 (Kabat 89-97) | AAWDASLRGV (SEQ ID NO: 16) |

In still other embodiments, the anti-FXII antibody or antigen binding fragment is chosen from the affinity matured (relative to 3F7) antibodies VR115, VR112, VR24, VR110, VR119.

| mAb | HCDR1 | HCDR2 | HCDR3 | LCDR1 | LCDR2 | LCDR3 |
|---|---|---|---|---|---|---|
| 3F7 | 9 | 10 | 12 | 14 | 15 | 16 |
| VR119 | 9 | 11 | 12 | 14 | 15 | 16 |
| VR112 | 9 | 11 | 12 | 14 | 15 | 16 |
| VR115 | 9 | 11 | 12 | 14 | 15 | 16 |
| VR24 | 9 | 10 | 12 | 18 | 15 | 16 |
| VR110 | 9 | 11 | 12 | 14 | 15 | 16 |

As noted above SEQ ID NO: 11 is a degenerate sequence. VR119 comprises SEQ ID NO: 11 wherein $X_1$ is N, $X_2$ is V, $X_3$ is P; $X_4$ is L, $X_5$ Y; and $X_6$ is G. VR112 comprises SEQ ID NO: 11 wherein $X_1$ is N, $X_2$ is V, $X_3$ is P, $X_4$ is V, $X_5$ is Q, and $X_6$ is G. VR115 comprises SEQ ID NO: 11 wherein $X_1$ is D, $X_2$ is I, $X_3$ is P, $X_4$ is T, $X_5$ is K, and $X_6$ is G. VR110 comprises SEQ ID NO: 11 wherein $X_1$ is D, $X_2$ is M, $X_3$ is P, $X_4$ is T, $X_5$ is K, and $X_6$ is G. VR24 comprises a unique LCDR1: SGSSEMTVHHYVY (SEQ ID NO: 18).

In embodiments involving antibody CDRs, CDR's are defined according to the KABAT numbering system. (Kabat E A, Wu T T, Perry H M, Gottesman K S, Foeller C (1991) Sequences of proteins of immunological interest, 5th edn. U.S. Department of Health and Human services, NIH, Bethesda, Md.)

In some embodiments, the antibody or antigen-binding fragment thereof is an anti-Factor XII/FXIIa monoclonal antibody or antigen-binding fragment thereof that inhibits Factor XIIa-alpha by more than 40%, more than 50%, or more than 60%, when used at a molar ratio of FXIIa-alpha to antibody of 1:0.2. In some embodiments, the antibody or antigen binding fragment thereof inhibits Factor XIIa-alpha by more than 80%, more than 85%, or more than 90%, at a molar ratio of FXIIa-alpha to antibody of 1:0.5. In one embodiment, the antibody achieves complete inhibition of FXIIa-alpha at a molar ratio of 1:0.5. In one embodiments, the FXIIa-alpha is human Factor XIIa-alpha. In one embodiment, the antibody or antigen binding fragment thereof has an affinity for human FXIIa that is at least comparable to antibody 3F7.

As discussed above, an "anti-FXII antibody" includes antibodies that bind to and inhibit either or both of FXII and FXIIa. In one embodiment, the antibody may be in the form of a full length Ig, Fab, F(ab)$_2$, Fv, scFv, or other form or variant thereof. The antibody may be monoclonal or polyclonal. The antibody may be characterized in that the isotype is IgM, IgD, IgA, IgG, or IgE, or any subclass thereof, such as IgG$_1$, or variants thereof. The antibody may be from a mammalian species, including, but not limited to human, mouse, rat, rabbit, goat, hamster, or monkey. The antibody may be humanized or CDR-grafted. The antibody maybe mutated or modified to alter immunogenicity, half-life, or to impart other advantageous properties associated with a therapeutic antibody. In one embodiment, the antibody is an anti-FXII antibody that binds to an epitope on the heavy chain or light chain of FXII (wherein, "FXII" includes FXII and FXIIa), such as a neutralizing epitope. The antibody may be high affinity and/or high avidity for binding to FXII. The antibody may be conjugated to a polypeptide, nucleic acid or small molecule.

In another embodiment, the FXII inhibitor is a protein, peptide, nucleic acid, or small molecule. The term "small molecule" refers to a low molecular weight compound. A small molecule may be for example less than 1000 daltons, allowing diffusion across cell membranes. A small molecule may be characterized in that it binds with high affinity to FXII. A preferred small molecule is one which can be absorbed from the GI tract.

E. FXII Inhibitors Linked to Half-Life Enhancing Polypeptides

Another aspect of the application provides FXII inhibitors linked to a half-life enhancing polypeptide (HLEP). In one embodiment, FXII inhibitors are small proteins. Therefore a rapid renal clearance as published for other small proteins can be expected. (Werle M and Bernkop-Schnurch A, Amino Acids 2006; 30:351-367.) One way to address a short plasma half-life of a polypeptidic compound is to inject it repeatedly or via continuous infusion. Another approach is to increase the intrinsic plasma half-life of the polypeptide itself. For example, in one embodiment, FXII inhibitors are linked to half-life extending proteins.

A "half-life enhancing polypeptide" increases the half-life of the FXII inhibitor in vivo in a patient or in an animal. For example, albumin and immunoglobulins and their fragments or derivatives have been described as half-life enhancing polypeptides (HLEPs). Ballance et al. (WO 2001/79271) described fusion polypeptides of a multitude of different therapeutic polypeptides which, when fused to human serum albumin, are predicted to have an increased functional half-life in vivo and extended shelf-life.

The terms "albumin" and "serum albumin" encompass human albumin (HA) and variants thereof, the full mature form of which is given (SEQ ID NO: 19), as well as albumin from other species and variants thereof. As used herein, "albumin" refers to an albumin polypeptide or amino acid sequence, or an albumin variant, having one or more functional activities (e.g. biological activities) of albumin. As used herein, albumin is capable of stabilizing or prolonging the therapeutic activity of a FXII inhibitor. The albumin may be derived from any vertebrate, especially any mammal, for example human, monkey, cow, sheep, or pig. Non-mammalian albumins include, but are not limited to, albumin from hen and salmon. The albumin portion of the albumin-linked polypeptide may be from a different animal than the therapeutic polypeptide portion. See WO 2008/098720 for examples of albumin fusion proteins.

In one embodiment, an albumin variant is at least 10, 20, 40, or at least 70 amino acids long or may include 15, 20, 25, 30, 50 or more contiguous amino acids from the human albumin (HA) sequence (e.g., the sequence set forth in FIG. 3, SEQ ID NO: 19 or may include part or all of specific domains of HA. An albumin variant may include an amino acid substitution, deletion, or addition, either conservative or non-conservative substitution, wherein such changes do not substantially alter the active site, or active domain, which confers the therapeutic activities of the half-life enhancing polypeptides. These variants may share 70%, 75%, 80%, 85%, 90%, 91%, 92%, 93%, 94%, 95%, 96%, 97%, 98% or 99% or any percentage in between homology.

In one embodiment, the albumin variant includes fragments and may consist of or alternatively comprise at least one whole domain of albumin or fragments of said domains, for example domains 1 (amino acids 1-194 of SEQ ID NO: 19), 2 (amino acids 195-387 of SEQ ID NO: 19), 3 (amino acids 388-585 of SEQ ID NO 19), 1+2 (1-387 of SEQ ID NO: 19), 2+3 (195-585 of SEQ ID NO: 19) or 1+3 (amino acids 1-194 of SEQ ID NO: 19+amino acids 388-585 of SEQ ID NO: 19). Each domain is itself made up of two homologous subdomains namely residues 1-105, 120-194, 195-291, 316-387, 388-491 and 512-585, of SEQ ID NO: 19, with flexible inter-subdomain linker regions comprising residues Lys106 to Glu119, Glu292 to Val315 and Glu492 to Ala511.

In another embodiment, other proteins that are structurally or evolutionarily related to albumin may be used as HLEPs, including, but not limited to alpha-fetoprotein (WO 2005/024044; Beattie and Dugaiczyk, 20 *Gene* 415-422, 1982), afamin (Lichenstein et al. 269 *J. Biol. Chem.* 18149-18154, 1994), and vitamin D binding protein (Cooke and David, 76 *J. Clin. Invest.* 2420-2424, 1985). Their genes represent a multigene cluster with structural and functional similarities mapping to the same chromosomal region in humans, mice, and rats. The structural similarity of the albumin family members suggests that they can be used as HLEPs. For example, alpha-fetoprotein has been claimed to extend the half-life of an attached therapeutic polypeptide in vivo (WO 2005/024044). Such proteins, or variants thereof, that are capable of stabilizing or prolonging therapeutic activity may be used, and may be derived from any vertebrate, especially any mammal, for example human, monkey, cow, sheep, or pig, or non-mammal including but not limited to, hen or salmon. (See WO 2008/098720.) Such variants may be of 10 or more amino acids in length or may include about 15, 20, 25, 30, 50 or more contiguous amino acids of the respective protein sequence or may include part or all of specific domains of the respective proteins. Albumin family member fusion proteins may include naturally occurring polymorphic variants.

In one embodiment, mono- or poly- (e.g., 2-4) polyethylene glycol (PEG) moieties may be used to extend half-lives. Pegylation may be carried out by any of the pegylation reactions available. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions will be determined case by case based on known parameters and the desired result. There are a number of PEG attachment methods known in the art. See, for example, EP 0 401 384; Malik et al., *Exp. Hematol.,* 20:1028-1035 (1992); Francis, *Focus on Growth Factors,* 3(2):4-10 (1992); EP 0 154 316; EP 0 401 384; WO 92/16221; WO 95/34326; U.S. Pat. No. 5,252,714.

In another embodiment, an immunoglobulin (Ig), or variants thereof, may be used as an HELP, wherein a variant includes fragments. In one embodiment, the Fc domain or portions of the immunoglobulin constant region are used. The constant region may be that of an IgM, IgG, IgD, IgA, or IgE immunoglobulin. The therapeutic polypeptide portion is connected to the Ig via the hinge region of the antibody or a peptide linker, which may be cleavable. Several patents and patent applications describe the fusion of therapeutic proteins to immunoglobulin constant regions to extend the therapeutic protein's half-life in vivo (US 2004/0087778, WO 2005/001025, WO 2005/063808, WO 2003/076567, WO 2005/000892, WO 2004/101740, U.S. Pat. No. 6,403, 077). Therefore, another embodiment is to use such immunoglobulin sequences, for example, Fc fragments of immunoglobulins and variants thereof, as HLEPs. Inhibitors of FXII may be fused to Fc domains or at least portions of immunoglobulin constant regions as HLEPs and may be produced as recombinant molecules in prokaryotic or eukaryotic host cells, such as bacteria, yeast, plant, animal (including insect) or human cell lines or in transgenic animals (WO 2008/098720).

An example of one SPINK mutant Fc fusion protein, the SPINK-K2-Fc fusion protein, is described in WO2008/098720.

F. Linkers

In one embodiment, an intervening peptidic linker may be introduced between the therapeutic polypeptide and the HLEP. In one embodiment, a cleavable linker is introduced, particularly if the HLEP interferes with the therapeutic polypeptide's specific activity, e.g. by steric hindrance. In certain embodiments, the linker is cleaved by enzymes such as coagulation proteases of the intrinsic, extrinsic, or common coagulation pathway. Coagulation proteases of the intrinsic pathway are proteases in the contact activation pathway, including, for example, FXIIa, FXIa, or FIXa. In one embodiment, the linker is cleaved by FXIIa. Proteases of the extrinsic pathway include proteases in the tissue factor pathway, for example, FVIIa. Proteases of the common pathway include proteases involved in the conversion of fibrinogen to fibrin, for example, FXa, FIIa, and FXIIIa.

G. Therapeutic Formulation and Administration

The FXII inhibitor or variant thereof may have a purity greater than 80%, or greater than 95%, 96%, 97%, 98%, or 99% purity. In one embodiment, the variant may have a pharmaceutically pure state that is greater than 99.9% pure with respect to contaminating macromolecules, such as other proteins and nucleic acids, and free of infectious and pyrogenic agents.

The purified FXII inhibitor may be dissolved in conventional physiologically compatible aqueous buffer solutions to which there may be added, optionally, pharmaceutical excipients to provide pharmaceutical preparations for preventing, treating, or ameliorating the effects of inflammatory demyelinating disease in a patient. Such pharmaceutical carriers and excipients as well as suitable pharmaceutical formulations are well known in the art. See for example Kibbe et al. Handbook of Pharmaceutical Excipients, (3$^{rd}$ ed., Pharmaceutical Press), 2000. The pharmaceutical composition may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

Formulations of the FXII inhibitor are delivered to the patient by any pharmaceutically suitable means of administration. Various delivery systems are known and can be used to administer the composition by any convenient route. The compositions may be administered systemically, such as parenterally. The term "parenteral" as used here includes intravenous, subcutaneous, intramuscular, intra-arterial and intra-tracheal injection; as well as instillation, spray application, and infusion techniques. Parenteral formulations may be administered intravenously or subcutaneously, either in bolus form or as a constant infusion, according to known procedures. Preferred liquid carriers, which are well known for parenteral use, include sterile water, saline, aqueous dextrose, sugar solutions, ethanol, glycols, and oils. For systemic use, the therapeutic proteins may be formulated for an intravenous line or an arterial line. The formulations may be administered continuously by infusion or by bolus injection.

In some embodiments, the formulations are administered by intrathecal injection or by intracranial injection, so that direct access is gained to the spinal cord and brain. In these embodiments, the formulation may be specially formulated; for example, the formulation may lack preservatives.

In some embodiments, the formulation is administered via intranasal administration. Intranasal delivery has been reported to enable the direct entry of viruses and macromolecules into the cerebrospinal fluid (CSF) or CNS. Mathison et al. J. Drug Target 1998; 5:415-41; Chou et al. Biopharm Drug Dispos. 1997; 18:335-46; Draghia et al., Gene Ther. 1995; 2(6):418-235. In one embodiment, a viral vector, such as an adenovirus vector, comprising a gene encoding any of the FXII inhibitors that are proteins may be delivered via olfactory receptor neurons to obtain expression of the encoded protein in the brain. Draghia et al., Gene Ther. 1995; 2(6):418-23.

Tablets and capsules for oral administration may contain conventional excipients such as binding agents, fillers, lubricants, or wetting agents, etc. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles, and preservatives. Some formulations encompass slow release systems, such as a patch.

The dose of the FXII inhibitor may depend on many factors such as, e.g., the indication, formulation, or mode of administration, and may be determined in preclinical and clinical trials for each respective indication. For example, in one embodiment, the dose of FXII inhibitor is 0.1 mg/kg, 1 mg/kg, 50 mg/kg, 100 mg/kg, 200 mg/kg, 500 mg/kg, 1000 mg/kg, or any dose in between, or from 0.1-1000 mg/kg, or 1-1000 mg/kg, or 1-500 mg/kg, or 50-500 mg/kg, 50-200 mg/kg, or 100-200 mg/kg, or any dose range in between.

In those embodiments involving a therapeutically effective dose of an anti-FXII antibody or antigen binding fragment, a therapeutically effective dose is a dose that brings about a positive therapeutic effect in the patient or subject requiring the treatment. A therapeutically effective dose is generally in the range of about 0.01 to 100 mg/kg, from about 0.01 to 50 mg/kg, from about 0.1 to 30 mg/kg, from about 0.1 to 10 mg/kg, from about 0.1 to 5 mg/kg, from about 0.1 to 2 mg/kg or from about 0.1 to 1 mg/kg, or any dose range in between, or one of the doses for a FXII inhibitor presented above or in the examples.

The treatment may comprise giving a single dose or multiple doses. If multiple doses are required, they may be administered daily, every other day, weekly, biweekly, monthly, or bimonthly or as required. A depository may also be used that slowly and continuously releases the antibody or antigen binding fragment thereof. A therapeutically effective dose may be a dose that inhibits FXIIa in the subject by at least 50%, preferably by at least 60%, 70%, 80%, 90%, more preferably by at least 95%, 99% or even 100% (or by any percentage in between).

The FXII inhibitor may be administered alone or in conjunction with other therapeutic agents. These agents may be co-formulated, or may be administered as separate formulations either concurrently or separately and via the same route of administration or different routes of administration. The schedule of administration or dose of a FXII inhibitor may also vary between individual patients with the same indication or different indications depending on factors such as other medical conditions or therapies.

The embodiments are further illustrated by the following examples which should not be construed as limiting. Other embodiments will be apparent to those skilled in the art from consideration of the specification and practice of the embodiments disclosed. The contents of all references, patents, and published patent applications cited throughout this application are hereby incorporated by reference.

EXAMPLES

Example 1: The Plasmatic Blood Coagulation System as an Innovative Target in Multiple Sclerosis Preliminary studies suggest that primary and secondary hemostasis are involved in the inflammatory neurodegeneration in MS. For example, it has recently been demonstrated in the EAE animal model that STIM1 and STIM2, which had already been identified as key molecules in $Ca^{2+}$-dependent platelet activation, represent important pathophysiological determinants of the inflammatory reaction and neurodegeneration. (Schuhmann et al., J. Immunol. 2010; 184:1536-42.) Furthermore, deposits of fibrinogen and fibrin are found in both the central vessels and the brain parenchyma of MS patients. (Sobel & Mitchell, Am. J. Pathol. 1989; 135:161-68; Claudio et al., Acta Neuropathol 1995; 90:228-38; Marik et al., Brain 2007; 130:2800-15.) Fibrin is the end product of so-called plasmatic blood coagulation system, which in turn is made up of the extrinsic and intrinsic systems. Coagulation Factor XII (FXII) is the starting point of the intrinsic blood coagulation cascade, which initially leads to activation of FXI. At the same time, it activates the proinflammatory contact (kinin) system, the end point of which is the formation of bradykinin.

Our work demonstrated that the bradykinin receptor B1R is an important regulator of inflammatory cell invasion in an EAE model. (Göbel et al., J. Autoimmun 2011:36:106-14.) B1R deficient mice experienced less severe EAE. Similarly, wildtype mice treated with a selective antagonist of B1R also experienced a lower disease maximum compared to untreated mice. In contrast, blockade of the bradykinin receptor B2R by disruption of the B2R gene did not alter the EAE disease course. Interestingly, B2R mediates the majority of effects of bradykinin, although both B1R and B2R mediate the classical inflammatory process after tissue injury. Further, the mechanism leading to bradykinin activity in vivo is unclear since bradykinin can be activated by at least two pathways: the intrinsic coagulation pathway and another pathway that must be FXII independent since it occurs even in FXII knockout mice. (Schmaier A H, Int. Immunopharmacol. 2008; 8:161-65.)

To test whether FXII also contributes to EAE, EAE was induced by immunization of 10-12 weeks old female C57Bl/6, FXII- or FXI-deficient mice with 200 µg $MOG_{35-55}$. The C57Bl/6 $MOG_{35-55}$ mouse model is commonly used for pre-clinical validation of therapeutic compounds. (Krishnamoorthy & Wekerle, Eur. J. Immunol 2009; 39:2031-35.) The course of EAE in this model resembles a primary progressive form of MS, since once induced the disease does not remit. Complete Freund's Adjuvant (CFA) was supplemented with MOG to obtain a 1 mg/ml emulsion and 2×100 µl were injected subcutaneously at two different sites of the flank of deeply anesthetized mice. Pertussis toxin was injected on the day of immunization and 2 d later (400 ng, Alexis, San Diego, Calif.). All animals were kept under standard conditions and had access to water and food ad libitum.

Pharmacological modulation was also performed using the FXII antagonist H-D-Pro-Phe-Arg-chloromethylketone (PCK) (8 µg/g; Bachem) administered by daily intravenous injection. PCK irreversibly inhibits the amidolytic activity of activated FXII (FXIIa) and plasma kallikrein-mediated activation of FXII. (Tans et al., Eur. J. Biochem. 1987; 164:637-42; Kleinschnitz, J Exp Med. 2006 Mar. 20; 203 (3):513-8.)

The clinical course of EAE was monitored daily by two blinded investigators using the following score system: grade 0, no abnormality; grade 1, limp tail tip; grade 2, limp tail; grade 3, moderate hind limb weakness; grade 4, complete hind limb weakness; grade 5, mild paraparesis; grade 6, paraparesis; grade 7, heavy paraparesis or paraplegia; grade 8, tetraparesis; grade 9, quadriplegia or premoribund state; grade 10, death. Animals, with a score higher than 7 were euthanized and continued with the accordant score until the end of the experiment.

In FXII-deficient mice the maximum disease rate was significantly reduced. (FIG. 4A.) Similar results were obtained in a pharmacological blockade with PCK. (FIG. 4C, 4D.) PCK had an effect even when treatment was started on day 12, when the animals already showed EAE symptoms (FIG. 4D). But in FXI-deficient mice, the EAE disease course was similar to that in the wildtype control mice. (FIG. 4B.) Since FXI is immediately downstream of FXII and is activated by FXIIa, these results indicate that it is not the role of FXII in the intrinsic coagulation cascade that led to the observed protective effect in the EAE model.

Figure 5:
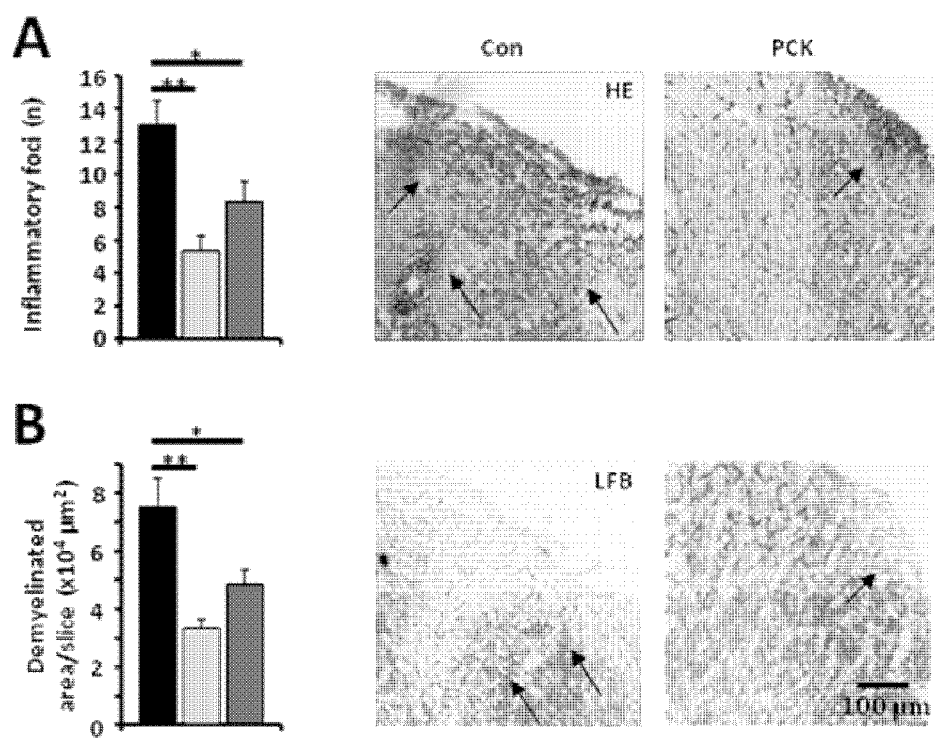
FIG. 5A-5E summarize histologic and in vitro functional data.
Figure 5:
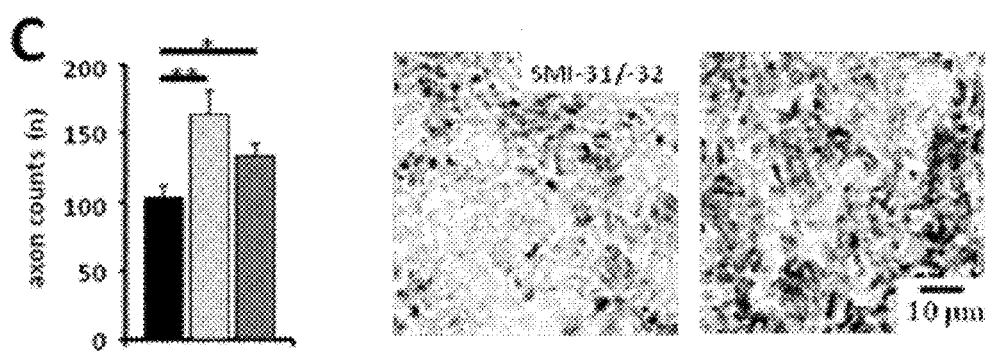

In addition to the reduction in disease score, the number of inflammatory foci and both demyelination and axonal damage were also significantly reduced in FXII-deficient animals. FIG. 5 depicts the number of inflammatory foci (FIG. 5A), demyelinated area/slice (FIG. 5B), and the axon counts (FIG. 5C) in control (left bar), PCK treated (middle bar), and FXII−/− mice (right bar). For quantification, stained sections were examined in a blinded fashion by microscopy (Axiophot2, Zeiss; Oberkochen, Germany) with a CCD camera (Visitron Systems; Tuchheim, Germany). Inflammatory foci (H&E), demyelinated areas (LFB), and cells were counted on five randomly selected samples utilizing MetVue Software (Molecular Devices; Downingtown, USA). The number of axons was analyzed in defined lesions. Fluorescence intensity was measured utilizing ImageJ (NIH, USA). Examples of histologic comparisons between control (Con) and PCK-treated mice are presented for each bar graph. Arrows show areas of inflammation (FIG. 5A), demyelination (FIG. 5B), and axonal damage (FIG. 5C).

In-vitro analyses also showed an altered immune response (FIGS. 5D and 5E). Splenocytes were isolated from immunized mice at the disease maximum and 50 days after EAE induction and stimulated with $MOG_{35-55}$ peptide (10 mg/ml) or CD3/CD28 beads (cell to bead ratio 2:1). For the proliferation assay shown in FIG. 5D, $1\times10^5$ splenocytes were cultured in 1 ml DMEM containing 10 mM HEPES, 25 mg/ml gentamicin, 50 mM mercaptoethanol, 5% FCS, 2 mM glutamine, and 1% nonessential amino acids (Cambrex; Verviers, Belgium) for three days and stimulated with CD3/CD28 beads (cell to bead ratio 2:1; Dynal Biotech, Hamburg, Germany) or 10 mg/ml $MOG_{35-55}$. $^3H$ thymidine (Amerham; Piscataway, N.J.) was added for the final 14 hours, and radioactivity was measured on a beta-scintillation counter (TopCount NXT; PerkinElmer, Rodgau-Jugesheim, Germany). Experiments were performed in quadruplicates.

As shown in FIG. 5D, the proliferation among control (left bar), PCK treated (middle bar), and FXII−/− mice (right bar) splenocytes stimulated with CD3/CD28 beads was not significantly different. When $MOG_{35-55}$ peptide was used to stimulate proliferation, there was a significant different between control and PCK-treated mice, but not between control and FXII−/− mice.

Supernatants of MOG restimulated splenocytes were also assessed for IFNγ, IL-17, IL-4 and IL-6 protein levels by ELISA (R&D Systems; Wiesbaden, Germany) according to the manufacturer's instructions. The results, presented in FIG. 5E, show that there was reduced production of IL-17, TNFα and IL-6 from splenocytes from both PCK treated (middle bar) and FXII−/− mice (right bar) compared to control. Levels of IFNγ were not significantly different.

Taken together, these results suggest that the inhibition of FXII leads to a change in the peripheral immune response that is not associated with the change in the intrinsic coagulation cascade.

Example 2: A Protein Inhibitor of FXII Also Inhibits Clinical Signs of Disease in a Primary Progressing Model of Neurological Autoimmune Inflammation rHA-Infestin-4, another inhibitor of FXII, was also active in the EAE model described in detail in Example 1. In this study, mice were treated with rHA-infestin-4, a protein comprising human albumin fused to the infestin 4 domain via a linker (which is described in Hagedorn et al. Circulation 2010; 121:1510-17) by daily intravenous injections at a dose of 200 µg/g.

As shown in FIG. 6A, rHA-Infestin-4 also reduced the EAE score early in the course of disease. And as was seen in the study in PCK-treated and FXII−/− mice, treatment with rHA-Infestin-4 resulted in a significant reduction in IL-17 production relative to control (FIG. 6B).

These results provide additional evidence that pharmacological blockade of FXII offers a new, alternative anti-inflammatory strategy for the treatment of MS.

Example 3: Anti-FXII Antibody Treatment Inhibits Clinical Signs of Disease in a Relapsing Model of Neurological Autoimmune Inflammation An anti-Factor XII antibody was also used to test the role of FXII in a second EAE model—female SJL mice immunized with PLP peptide (Myelin Proteolipid Protein). This EAE mouse model replicates many of the clinical and histopathological signs of MS including degeneration of motor neuron function. Like the C57Bl/6 MOG$_{35-55}$ model, SJL mice immunized with PLP is an accepted model for use in pre-clinical validation of therapeutic compounds. (Krishnamoorthy & Wekerle, Eur. J. Immunol 2009; 39:2031-35.) The SJL PLP model, however, also experiences remission and relapse, as occurs in the relapsing remitting form of MS.

EAE was induced in female SJL mice aged 8-12 weeks by immunizing them subcutaneously with 100 μg of PLP peptide (139-151) (Mimotopes, Clayton, Vic, Australia) emulsified in Complete Freund's adjuvant (CFA) (Difco, BD San Diego, Calif., USA), followed by 200 ng pertussis toxin (Sigma-Aldrich, St Louis, Mo., USA) administered intravenously on day 0. On day "−1" (i.e., the day before EAE induction injection), and on days 1, 3, 6, 8, 10, 13, and 15 following induction, control animals were given a subcutaneous injection of 200 μg of isotype control monoclonal antibody while the experimental group received anti-FXII mAb (3F7). Disease was monitored from day 0 to 15. Clinical score was assessed as described in Langrish et al., J Exp Med. 2005; 201:233-40, with a maximum score of 6 for each mouse. All animal procedures were approved by the CSL animal ethics committee.

Figure 7:
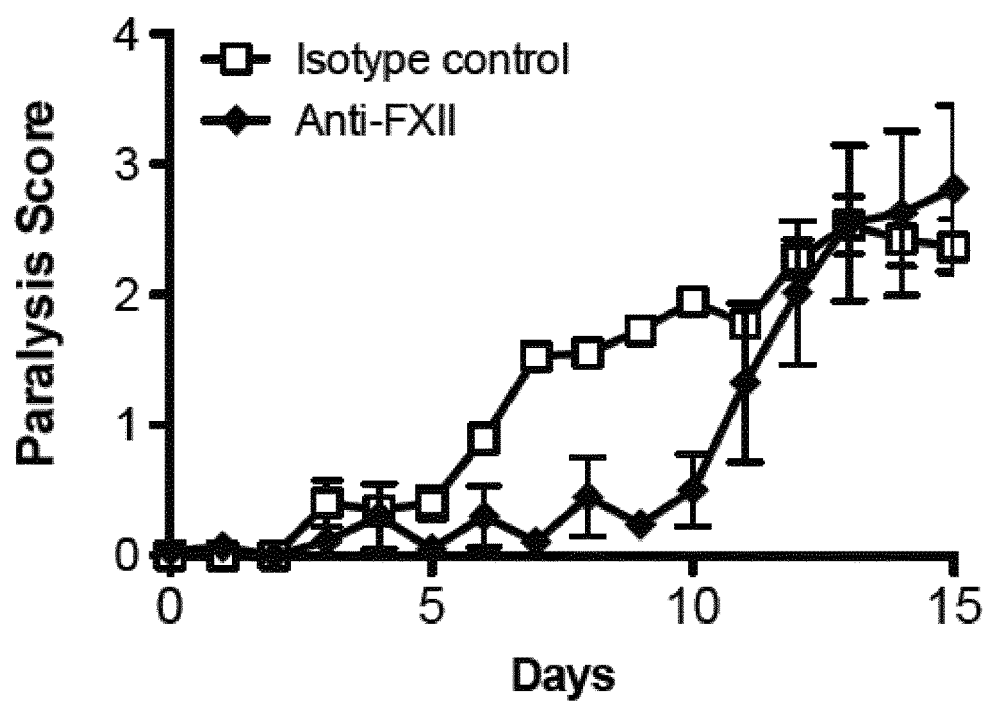
FIG. 7 presents the paralysis score as a function of time for mice treated with an anti-Factor XII antibody (filled diamonds) or with an isotype control antibody (open squares).

Treatment of mice with a neutralizing anti-FXII monoclonal antibody (mAb) inhibited the clinical progression of EAE in this relapsing model (FIG. 7). Inhibition was most effective at the early stage of disease.

Figure 8:
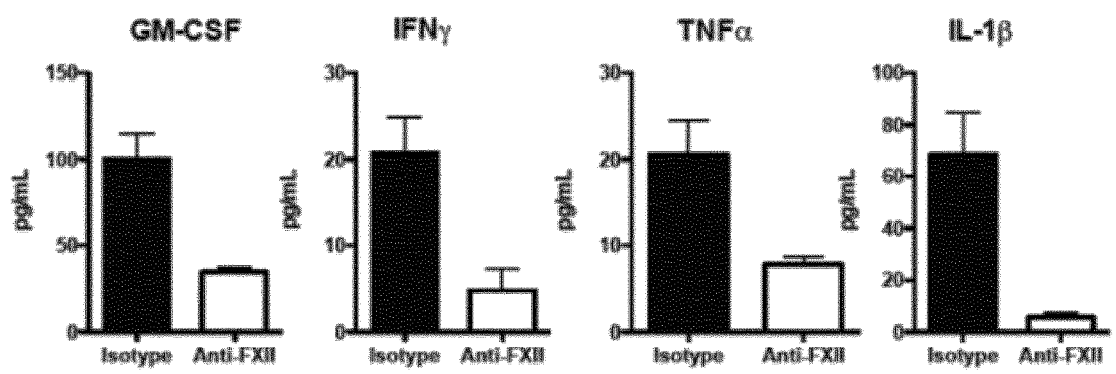
FIG. 8 presents the cytokine levels in the blood of anti-FXII treated and control mice for the cytokines GM-CSF, IFNγ, TNFα and, IL-β.

To assess the effect of FXII blockade on proinflammatory cytokine responses in-vivo, animals were bled at day 9 and serum harvested for cytokine analysis by Luminex assay (Millipore, Billerica, Mass., USA) on a Luminex 200 instrument (Austin, Tex., USA) according the manufacturer's instructions. Anti-FXII antibody treatment led to a reduction in pro-inflammatory cytokine release into the blood. As shown in FIG. 8, anti-FXII reduced levels of GM-CSF, IFNγ, TNFα and IL-1β.

Macrophages and dendritic cells (DCs) are prominent in EAE and MS inflammatory lesions and have roles in mediating tissue injury. They contribute by production of proinflammatory cytokines, antigen presentation to auto-reactive lymphocytes, and in the production of reactive oxygen species that cause direct myelin damage (Graham et. al., 2009). Chemerin is a molecule that circulates as a zymogen within the blood, and is activated by serine proteases which include plasmin, neutrophil elastase, and to a lesser extent FVIIa. FXIIa, however, is the predominant activator (Qu and Chaikof, 2010). Activated chemerin is a potent chemoattractant for cells expressing chemokine-like receptor 1 (CMKLR1), also known as ChemR23. This receptor is highly expressed by plasmacytoid dendritic cells (pDC), tissue resident macrophages, monocytes, and NK cells (Hart and Greaves, 2010). Studies by Graham et al. (2009), have shown that mouse knockouts of the chemerin receptor, CMKLR1, or Chem23, have overall lower clinical scores in EAE experiments. Accordingly, it is possible that, at least in the relapsing EAE model, blocking the action of FXII with an antibody may act, at least in part, by reducing the amount of active chemerin, thereby producing a therapeutic effect in the EAE experiments.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for treatment and/or amelioration of multiple sclerosis comprising administering to a subject in need thereof a therapeutically effective amount of a direct inhibitor of Factor XII (FXII), wherein the direct inhibitor of FXII contacts FXII to inhibit the activity and/or activation of FXII in the subject.

2. The method of claim 1, wherein the direct inhibitor of FXII comprises the wild type infestin-4 polypeptide sequence (SEQ ID NO: 2), or a variant thereof, wherein the variant comprises:
(a) the N-terminal amino acids 2-13 of SEQ ID NO: 2 and at least one and up to five amino acid mutations outside said N-terminal amino acids that result in differences from the wild type infestin-4 sequence; and/or
(b) the six conserved cysteine residues of the wild type Infestin-4 polypeptide sequence (SEQ ID NO: 2) and homology of at least 70% to the wild type Infestin-4 polypeptide sequence.

3. The method of claim 1, wherein the direct inhibitor of FXII comprises wild-type SPINK-1 sequence (SEQ ID NO: 3), which is mutated to include the N-terminal amino acids 2-13 of SEQ ID NO: 2, or a variant of said mutated SPINK-1, wherein the variant comprises:
(a) the N-terminal amino acids 2-13 of SEQ ID NO: 2 and at least one and up to five amino acid mutations outside said N-terminal amino acids that result in differences from the wild type SPINK-1 sequence and which increase the homology of the variant to the wild type infestin-4 sequence; and/or
(b) the six conserved cysteine residues of the wild-type SPINK-1 sequence (SEQ ID NO: 3) and homology of at least 70% to the wild type SPINK-1 sequence.

4. The method of claim 3, wherein the direct inhibitor of FXII comprises wild type SPINK-1 (SEQ ID NO: 3), SPINK-1 mutant K1 (SEQ ID NO: 4), SPINK-1 mutant K2 (SEQ ID NO: 5) or SPINK-1 mutant K3 (SEQ ID NO: 6).

5. The method of claim 1, wherein the direct inhibitor of FXII comprises an anti-FXII antibody or antigen binding fragment.

6. The method of claim 5, wherein the anti-FXII antibody or antigen binding fragment thereof comprises (a) a VH region comprising heavy chain CDR1 as set forth in SEQ ID NO: 9, heavy chain CDR2 as set forth in SEQ ID NO: 11, and heavy chain CDR3 as set forth in SEQ ID NO: 13; and/or (b) a VL region comprising light chain CDR1 as set forth in SEQ ID NO: 14, light chain CDR2 as set forth in SEQ ID NO: 15, and light chain CDR3 as set forth in SEQ ID NO: 17.

7. The method of claim 5, wherein the anti-FXII antibody or antigen-binding fragment thereof comprises (a) a VH region comprising heavy chain CDR1 as set forth in SEQ ID NO: 9, heavy chain CDR2 as set forth in SEQ ID NO: 10, and heavy chain CDR3 as set forth in SEQ ID NO: 12; and/or (b) a VL region comprising light chain CDR1 as set forth in SEQ ID NO: 14, light chain CDR2 as set forth in SEQ ID NO: 15, and light chain CDR3 as set forth in SEQ ID NO: 16.

8. The method of claim 5, wherein the anti-FXII antibody or antigen-binding fragment thereof comprises a VH region comprising SEQ ID NO: 7 and a VL region comprising SEQ ID NO: 8.

9. The method of claim 5, wherein the anti-FXII antibody is an IgG.

10. The method of claim 1, wherein the direct inhibitor of FXII is linked to a half-life enhancing polypeptide that is albumin, afamin, alpha-fetoprotein, vitamin D binding protein, human albumin or a variant thereof, an immunoglobulin or a variant thereof, or an Fc of an IgG.

11. The method of claim 10, wherein the half-life enhancing polypeptide is linked to the direct inhibitor of FXII via a linker.

12. The method of claim 11, wherein the linker is
(a) cleavable;
(b) cleavable by a coagulation protease of the intrinsic, extrinsic, or common coagulation pathway; and/or
(c) cleavable by Factor XIIa.

13. The method of claim 10, wherein the half-life enhancing polypeptide is human albumin or a variant thereof.

14. The method of claim 1, wherein the multiple sclerosis is relapsing remitting multiple sclerosis or primary progressing multiple sclerosis.

\* \* \* \* \*

SEQUENCE LISTING

```
<160> NUMBER OF SEQ ID NOS: 19

<210> SEQ ID NO 1
<211> LENGTH: 409
<212> TYPE: PRT
<213> ORGANISM: Triatoma infestans

<400> SEQUENCE: 1

Met Arg Tyr Leu Leu Leu Leu Gly Leu Ala Ala Phe Ser Ala Val Ser
1               5                  10                  15

Ala Glu Lys Lys Asp Pro Pro Cys Val Cys Pro Leu Ile Trp Lys Pro
            20                  25                  30

Val Cys Gly Ser Asp Gly Gln Thr Tyr Pro Ser Glu Cys Ile Leu Asn
        35                  40                  45

Cys Val Lys Tyr Ala Leu Lys Lys Asp Ile Lys Val Ala Tyr Gln Gly
    50                  55                  60

Ile Cys Lys His Val Thr Phe Ala Ala Glu Glu Gln Glu Val Glu
65                  70                  75                  80

Gly Trp Lys Gly Pro Cys Glu Cys Pro Arg Ala Leu His Arg Val Cys
            85                  90                  95

Gly Ser Asp Gly Asn Thr Tyr Ser Asn Pro Cys Thr Leu Asn Cys Ala
        100                 105                 110

Lys His Glu Arg Lys Ser Asp Leu Val Gln Val His Glu Gly Pro Cys
    115                 120                 125

Ser Pro Asp Glu His Glu Phe Glu Asp Pro Cys Glu Cys Asp Asn Lys
130                 135                 140
```

```
Phe Asp Pro Val Cys Gly Thr Gly Glu Val Thr Tyr Arg Asn Leu Cys
145                 150                 155                 160

His Leu Glu Cys Ala Thr Phe Thr Thr Ser Pro Gly Val Glu Val Asp
                165                 170                 175

Tyr Glu Gly Glu Cys Leu Ala Glu Thr Val Leu Leu Glu Glu Asn His
            180                 185                 190

Cys Ala Cys Pro Arg Val Leu His Arg Val Cys Gly Ser Asp Gly Asn
        195                 200                 205

Thr Tyr Ser Asn Pro Cys Thr Leu Asp Cys Ala Lys His Glu Gly Lys
    210                 215                 220

Pro Asp Leu Val Gln Val His Glu Gly Pro Cys Asp Pro Asn Asp His
225                 230                 235                 240

Asp Phe Glu Asp Pro Cys Glu Cys Asp Asn Lys Phe Glu Pro Val Cys
                245                 250                 255

Gly Thr Asp His Ile Thr Tyr Ser Asn Leu Cys His Leu Glu Cys Ala
            260                 265                 270

Ala Phe Thr Thr Ser Pro Gly Val Glu Val Lys Tyr Glu Gly Glu Cys
        275                 280                 285

His Ala Glu Ile Met Glu Gln His Gln Ile Leu Lys Ser Cys Ile Cys
    290                 295                 300

Thr Lys Met Tyr Lys Pro Val Cys Gly Thr Asp Gly His Thr Tyr Pro
305                 310                 315                 320

Asn Leu Cys Val Leu Lys Cys Arg Ile Ser Ser Lys Pro Gly Leu Lys
                325                 330                 335

Leu Ala His Val Gly Lys Cys Gly Ile Gly Leu Leu Ala Val Glu Thr
            340                 345                 350

Lys Glu Val Arg Asn Pro Cys Ala Cys Phe Arg Asn Tyr Val Pro Val
        355                 360                 365

Cys Gly Ser Asp Gly Lys Thr Tyr Gly Asn Pro Cys Met Leu Asn Cys
    370                 375                 380

Ala Ala Gln Thr Lys Val Pro Gly Leu Lys Leu Val His Lys Gly Arg
385                 390                 395                 400

Cys Gln Arg Ser Asp Val Glu Gln Phe
                405

<210> SEQ ID NO 2
<211> LENGTH: 48
<212> TYPE: PRT
<213> ORGANISM: Triatoma infestans

<400> SEQUENCE: 2

Glu Val Arg Asn Pro Cys Ala Cys Phe Arg Asn Tyr Val Pro Val Cys
1                   5                   10                  15

Gly Ser Asp Gly Lys Thr Tyr Gly Asn Pro Cys Met Leu Asn Cys Ala
                20                  25                  30

Ala Gln Thr Lys Val Pro Gly Leu Lys Leu Val His Glu Gly Arg Cys
            35                  40                  45

<210> SEQ ID NO 3
<211> LENGTH: 56
<212> TYPE: PRT
<213> ORGANISM: Homo sapiens

<400> SEQUENCE: 3

Asp Ser Leu Gly Arg Glu Ala Lys Cys Tyr Asn Glu Leu Asn Gly Cys
1                   5                   10                  15
```

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
            35                  40                  45

Leu Ile Gln Lys Ser Gly Pro Cys
    50                  55

<210> SEQ ID NO 4
<211> LENGTH: 53
<212> TYPE: PRT
<213> ORGANISM: Homo sapiens

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
            35                  40                  45

Lys Ser Gly Pro Cys
    50

<210> SEQ ID NO 5
<211> LENGTH: 53
<212> TYPE: PRT
<213> ORGANISM: Homo sapiens

<400> SEQUENCE: 5

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
            35                  40                  45

Lys Glu Gly Pro Cys
    50

<210> SEQ ID NO 6
<211> LENGTH: 54
<212> TYPE: PRT
<213> ORGANISM: Homo sapiens

<400> SEQUENCE: 6

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Asn Cys Ala Glu Asn Arg Lys Arg Gln Thr Ser Ile Leu Ile
            35                  40                  45

Gln Lys Glu Gly Pro Cys
    50

<210> SEQ ID NO 7
<211> LENGTH: 129
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Arg Pro Ser Gly Gly Thr Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser
```

```
<210> SEQ ID NO 8
<211> LENGTH: 110
<212> TYPE: PRT
<213> ORGANISM: Homo sapiens

<400> SEQUENCE: 8

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110
```

```
<210> SEQ ID NO 9
<211> LENGTH: 5
<212> TYPE: PRT
<213> ORGANISM: Homo sapiens

<400> SEQUENCE: 9

Lys Tyr Ile Met Gln
1               5
```

```
<210> SEQ ID NO 10
<211> LENGTH: 17
<212> TYPE: PRT
<213> ORGANISM: Homo sapiens

<400> SEQUENCE: 10

Gly Ile Arg Pro Ser Gly Gly Thr Thr Val Tyr Ala Asp Ser Val Lys
1               5                   10                  15

Gly
```

```
<210> SEQ ID NO 11
```

```
<211> LENGTH: 17
<212> TYPE: PRT
<213> ORGANISM: Artificial
<220> FEATURE:
<223> OTHER INFORMATION: Heavy chain CDR2 showing variations
<220> FEATURE:
<221> NAME/KEY: variant
<222> LOCATION: (3)..(3)
<223> OTHER INFORMATION: Xaa is selected from Arg, Asn, and Asp
<220> FEATURE:
<221> NAME/KEY: variant
<222> LOCATION: (4)..(4)
<223> OTHER INFORMATION: Xaa is selected from Pro, Val, Ile and Met
<220> FEATURE:
<221> NAME/KEY: variant
<222> LOCATION: (5)..(5)
<223> OTHER INFORMATION: Xaa is selected from Ser, Pro and Ala
<220> FEATURE:
<221> NAME/KEY: variant
<222> LOCATION: (6)..(6)
<223> OTHER INFORMATION: Xaa is selected from Gly, Leu, Val and Thr
<220> FEATURE:
<221> NAME/KEY: variant
<222> LOCATION: (7)..(7)
<223> OTHER INFORMATION: Xaa is selected from Gly, Tyr, Gln, Lys, Arg,
      Asn and Met
<220> FEATURE:
<221> NAME/KEY: variant
<222> LOCATION: (8)..(8)
<223> OTHER INFORMATION: Xaa is selected from Thr, Gly and Ser

<400> SEQUENCE: 11

Gly Ile Xaa Xaa Xaa Xaa Xaa Xaa Thr Val Tyr Ala Asp Ser Val Lys
1               5                   10                  15

Gly

<210> SEQ ID NO 12
<211> LENGTH: 20
<212> TYPE: PRT
<213> ORGANISM: Homo sapiens

<400> SEQUENCE: 12

Ala Leu Pro Arg Ser Gly Tyr Leu Ile Ser Pro His Tyr Tyr Tyr Tyr
1               5                   10                  15

Ala Leu Asp Val
            20

<210> SEQ ID NO 13
<211> LENGTH: 20
<212> TYPE: PRT
<213> ORGANISM: Artificial
<220> FEATURE:
<223> OTHER INFORMATION: Heavy chain CDR3 showing variations
<220> FEATURE:
<221> NAME/KEY: variant
<222> LOCATION: (9)..(9)
<223> OTHER INFORMATION: Xaa is selected from Ala, Met and Val
<220> FEATURE:
<221> NAME/KEY: variant
<222> LOCATION: (10)..(10)
<223> OTHER INFORMATION: Xaa is selected from Ser and Lys
<220> FEATURE:
<221> NAME/KEY: variant
<222> LOCATION: (11)..(11)
<223> OTHER INFORMATION: Xaa is selected from Pro, Lys, Thr and His
<220> FEATURE:
<221> NAME/KEY: variant
<222> LOCATION: (12)..(12)
<223> OTHER INFORMATION: Xaa is selected from His, Asn, Gly and Gln

<400> SEQUENCE: 13

Ala Leu Pro Arg Ser Gly Tyr Leu Xaa Xaa Xaa Xaa Tyr Tyr Tyr Tyr
```

```
                1               5                  10                  15

Ala Leu Asp Val
            20

<210> SEQ ID NO 14
<211> LENGTH: 13
<212> TYPE: PRT
<213> ORGANISM: Homo sapiens

<400> SEQUENCE: 14

Ser Gly Ser Ser Ser Asn Ile Gly Arg Asn Tyr Val Tyr
1               5                   10

<210> SEQ ID NO 15
<211> LENGTH: 7
<212> TYPE: PRT
<213> ORGANISM: Homo Sapiens

<400> SEQUENCE: 15

Ser Asn Asn Gln Arg Pro Ser
1               5

<210> SEQ ID NO 16
<211> LENGTH: 10
<212> TYPE: PRT
<213> ORGANISM: Homo sapiens

<400> SEQUENCE: 16

Ala Ala Trp Asp Ala Ser Leu Arg Gly Val
1               5                   10

<210> SEQ ID NO 17
<211> LENGTH: 10
<212> TYPE: PRT
<213> ORGANISM: Homo sapiens
<220> FEATURE:
<221> NAME/KEY: variant
<222> LOCATION: (2)..(2)
<223> OTHER INFORMATION: Xaa is selected from Ala and Ser
<220> FEATURE:
<221> NAME/KEY: variant
<222> LOCATION: (4)..(6)
<223> OTHER INFORMATION: Xaa can be any amino acid
<220> FEATURE:
<221> NAME/KEY: variant
<222> LOCATION: (7)..(7)
<223> OTHER INFORMATION: Xaa is selected from Leu and Val
<220> FEATURE:
<221> NAME/KEY: variant
<222> LOCATION: (9)..(10)
<223> OTHER INFORMATION: Xaa can be any amino acid

<400> SEQUENCE: 17

Ala Xaa Trp Xaa Xaa Xaa Xaa Arg Xaa Xaa
1               5                   10

<210> SEQ ID NO 18
<211> LENGTH: 13
<212> TYPE: PRT
<213> ORGANISM: Homo sapiens

<400> SEQUENCE: 18

Ser Gly Ser Ser Glu Met Thr Val His His Tyr Val Tyr
1               5                   10

<210> SEQ ID NO 19
<211> LENGTH: 585
```

<212> TYPE: PRT
<213> ORGANISM: Homo sapiens

<400> SEQUENCE: 19

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Lys Gln Leu Gly Glu
385                 390                 395                 400
```

-continued

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Lys His Pro Glu Ala Lys Arg Met Pro Cys
            435             440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```